United States Patent
Lee et al.

(10) Patent No.: US 9,956,251 B2
(45) Date of Patent: May 1, 2018

(54) PREPARATION METHOD FOR THERAPEUTIC AGENT OF BEAD-TYPE CHONDROCYTE

(71) Applicant: BIO SOLUTION CO., LTD., Seoul (KR)

(72) Inventors: Jung Sun Lee, Seoul (KR); Jin Yeon Lee, Gyeonggi-do (KR); Byung Chul Chae, Seoul (KR); Young Sook Son, Seoul (KR); Song Sun Chang, Seoul (KR)

(73) Assignee: BIO SOLUTION CO., LTD., Seoul (KR)

( * ) Notice: Subject to any disclaimer, the term of this patent is extended or adjusted under 35 U.S.C. 154(b) by 0 days. days.

(21) Appl. No.: 14/901,635

(22) PCT Filed: Jul. 23, 2014

(86) PCT No.: PCT/KR2014/006680
§ 371 (c)(1),
(2) Date: Dec. 28, 2015

(87) PCT Pub. No.: WO2015/012582
PCT Pub. Date: Jan. 29, 2015

(65) Prior Publication Data
US 2016/0367601 A1 Dec. 22, 2016

(30) Foreign Application Priority Data
Jul. 24, 2013 (KR) ........................ 10-2013-0087533

(51) Int. Cl.
*A61K 35/32* (2015.01)
*C12N 5/00* (2006.01)
*C12N 5/077* (2010.01)
*A61K 35/28* (2015.01)

(52) U.S. Cl.
CPC .............. *A61K 35/32* (2013.01); *A61K 35/28* (2013.01); *C12N 5/0062* (2013.01); *C12N 5/0655* (2013.01); *C12N 2500/90* (2013.01); *C12N 2513/00* (2013.01)

(58) Field of Classification Search
CPC .... A61K 35/32; C12N 5/0655; C12N 5/0062; C12N 2513/00; C12N 5/00; C12N 5/077; C12N 5/02
USPC .................................................. 435/383, 325
See application file for complete search history.

(56) References Cited

FOREIGN PATENT DOCUMENTS

| KR | 10-2005-0044849 | 5/2005 | ............... C12N 5/06 |
| WO | WO 98/32333 | 7/1988 | ............... A01N 1/02 |
| WO | WO 00/17321 | 3/2000 | ............... C12N 5/00 |

OTHER PUBLICATIONS

Adkisson, H.D., et al. "In vitro generation of scaffold independent neocartilage." *Clin Orthop*, 391S:S280-94, 2001.
Anderer, U., et al. "In vitro engineering of human autologous cartilage." *J Bone Miner Res*, 17: 1420-29, 2002.
Brittberg, M., et al. "Treatment of deep cartilage defects in the knee with autologous chondrocyte transplantation." *N Engl J Med.*, 331(14):889-95, Oct. 6, 1994.
Cancedda, R., et al. "Tissue engineering and cell therapy of cartilage and bone." *Matrix Biology*, 22:81-91, 2003.
Choi, Y.Y., et al. "Controlled size embryoid body formation in concave microwell arrays." *Biomaterials*, 31:4296-303, 2010.
Croucher, L.J., et al. "Extracellular ATP and UTP stimulate cartilage proteoglycan and collagen accumulation in bovine articular chondrocyte pellet cultures." *Biochim Biophys Acta*, 1502:297-306, 2000.
Fukuda, J., et al. "Orderly arrangement of hepatocyte spheroids on a microfabricated chip." *Tissue Eng*, 11:1254-62, 2005.
Graff, R.D., et al. "ATP release by mechanically loaded porcine chondrons in pellet culture." *Arthritis Rheum*, 43:1571-9, 2000.
Grande, D.A., et al. "Evaluation of matrix scaffolds for tissue engineering of articular cartilage grafts." *J Biomed Mater Res*, 34:211-20, 1997.
Grogan, S.P., et al. "A static, closed and scaffold-free bioreactor system that permits chondrogenesis in vitro." *Osteoarthritis Cartilage*, 11:403-11, 2003.
Hutmacher, D.W. "Scaffolds in tissue engineering bone and cartilage." *Biomaterials*, 21:2529-43, 2000.
Imabayashi, H., et al. "Redifferentiation of dedifferentiated chondrocytes and chondrogenesis of human bone marrow stromal cells via chondrosphere formation with expression profiling by large-scale cDNA analysis." *Exp Cell Res*, 288(1):35-50 2003.
Jain, R.K., et al., "Engineering vascularized tissue." *Nat Biotechnol*, 23:821-3, 2005.

(Continued)

*Primary Examiner* — Scott Long
*Assistant Examiner* — Paul C Martin
(74) *Attorney, Agent, or Firm* — Harness, Dickey & Pierce, P.L.C.

(57) ABSTRACT

The present invention relates to a preparation method for a therapeutic agent of a bead-type chondrocyte and, more specifically, to: a preparation method for a therapeutic agent of a bead-type chondrocyte without a support, comprising the steps of: a) dispensing chondrocytes and/or cells having chondrogenic differentiation capability in a 96-well deep well plate having a V-shaped bottom; b) centrifuging the plate; c) three-dimensionally culturing the plate in an incubator; and d) recovering pellets from each well, thereby being capable of easily and stably preparing cartilage tissues of a uniform quality, in large quantities; and a therapeutic agent of a bead-type chondrocyte without a support, prepared by the method, having effectiveness to repair damage by simply being implanted into cartilage damage by injection.

10 Claims, 19 Drawing Sheets
(19 of 19 Drawing Sheet(s) Filed in Color)

(56) References Cited

OTHER PUBLICATIONS

Landry, J., et al. "Regulatory mechanisms in spheroidal aggregates of normal and cancerous cells." *Recent Results Cancer Res*, 95: 50-66, 1984.
Landry, J., et al. "Spheroidal aggregate culture of rat liver cells: histotypic reorganization, biomatrix deposition, and maintenance of functional activities." *J Cell Biol*, 101: 914-23, 1985.
Larson, C.M., et al. "Retention of the native chondrocyte pericellular matrix results in significantly improved matrix production." *Matrix Biol*, 21:349-59, 2002.
Marlovits, S., et al. "Chondrogenesis of aged human articular cartilage in a scaffold-free bioreactor." *Tissue Eng*, 9:1215-26, 2003.
Mauck, R. L., et al. "Chondrogenic differentiation and functional maturation of bovine mesenchymal stem cells in long-term agarose culture." *OsteoArthritis and Cartilage*, vol. 4, pp. 179-189, 2006.
Moscona, A. "Rotation-mediated histogenetic aggregation of dissociated cells. A quantifiable approach to cell interactions in vitro." *Exp Cell Res*, 22: 455-475, 1961.
Naumann, A., et al. "Tissue engineering of autologous cartilage grafts in three-dimensional in vitro macroaggregate culture system." *Tissue Eng*, 10(11-12):1695-706, 2004.
Nehrer, S., et al. "Chondrocyte seeded collagen matrices implanted in a chondral defect in a canine model." Biomaterials, 19:2313-28, 1998.
Nishimoto, S., et al. "Effect of Chondroitin Sulfate and Hyaluronic Acid on Gene Expression in a Three-Dimensional Culture of Chondrocytes." *Journal of Bioscience and Bioengineering*, vol. 100, No. 1, pp. 123-126, 2005.
Ochi, M., et al. "Current concepts in tissue engineering technique for repair of cartilage defect." *Artif Organs*, 25:172-9, 2001.
Park, K., et al. "Scaffold-free, engineered porcine cartilage construct for cartilage defect repair—in vitro and in vivo study." Artif Organs, 30(8): 586-96, 2006.
Penick, K. J., et al. "High-throughput aggregate culture system to assess the chondrogenic potential of mesenchymal stem cells." *Bio Techniques*, vol. 39, No. 5, pp. 687-690, 2005.
Pittenger, M.F., et al. "Multilineage potential of adult human mesenchymal stem cells." *Science*, 284(5411):143-7, 1999.
Reginato, A.M., et al. "Formation of nodular structures resembling mature articular cartilage in long-term primary cultures of human fetal epiphyseal chondrocytes on a hydrogel substrate." *Arthritis Rheumm*, 7:1338-49, 1994.
Rouwkema, J. et al. "Vascularization in tissue engineering." *Trends Biotechnol* 26:434, 2008.
Schon, B. S., et al. "Validation of a high-throughput microtissue fabrication process for 3D assembly of tissue engineered cartilage constructs." *Cell Tissue Res*, vol. 347, pp. 629-642, 2012.
Sims, C.D., et al."Tissue engineered neocartilage using plasma derived polymer substrates and chondrocytes." *Plast Reconstr Surg*, 101:1580-5, 1998.
Sittinger, M., et al."Resorbable polyesters in cartilage engineering: affinity and biocompatibility of polymer fiber structures to chondrocytes." *J Biomed Mater Res* 33:57-63, 1996.
Stewart, M.C., et al. "Phenotypic stability of articular chondrocytes in vitro: the effects of culture models, bone morphogenetic protein 2, and serum supplementation." *J Bone Miner Res*, 15(1):166-74, Jan. 2000.
Tavella, S. et al. "Regulated expression of fibronectin, laminin and related integrin receptors during the early chondrocyte differentiation." *J Cell Sci*, 110:2261-70, 1997.
Wolf, F., et al. "Cartilage tissue engineering using pre-aggregated human articular chondrocytes." *European Cells and Materials*, 16:92-99, 2008.
Wong, S.F., et al. "Concave microwell based size-controllable hepatosphere as a three-dimensional liver tissue model." *Biomaterials*, 32(32):8087-96, Nov. 2011.
Zhang, Z., et al. "Hyaline cartilage engineered by chondrocytes in pellet culture: histological, immunohistochemical and ultrastructural analysis in comparison with cartilage explants." *J Anat*, 205:229-37, 2004.
International Search Report (ISR) dated Oct. 30, 2014 in PCT/KR2014/006680 published as WO 2015/012582 with English Translation.
Johnstone, B., Johnstone, B., et al., (1998). "In vitro chondrogenesis of bone marrow-derived mesenchymal progenitor cells". *Experimental Cell Research*. 238:265-272.
European Search Report dated Jan. 26, 2017 issued in EP 14829150.

Well cross section

96-Well plate (1 x 10⁵ cells/well) having flat bottom, 1ˢᵗ week 96-well deep well plate (1 x 10⁵ cells/well) having concave bottom Well cross section 96-well deep well plate (1 x 10⁵ cells/well) having V-shapped bottom, 3rd day Well cross section

PREPARATION METHOD FOR THERAPEUTIC AGENT OF BEAD-TYPE CHONDROCYTE

CROSS-REFERENCE TO RELATED APPLICATIONS

This application is a national phase application of PCT Application No. PCT/KR2014/006680, filed on Jul. 23, 2014, which claims benefit of Korean Patent Application 10-2013-0087533, filed on Jul. 24, 2013. The entire disclosure of the application identified in this paragraph is incorporated herein by reference.

FIELD

The present invention relates to a method for preparing a therapeutic agent of bead-type chondrocyte. More specifically, the present invention relates to a method for preparing a therapeutic agent of bead-type chondrocyte without a scaffold which comprises the steps of: a) dispensing chondrocyte and/or cell having chondrogenic potential into a 96-well deep well plate having V-shaped bottom; b) centrifuging the plate; c) three-dimensionally culturing the plate in an incubator; and d) collecting a pellet from each well, thereby being able to easily and stably prepare uniform, high-quality cartilage tissues with repetitive reproducibility in large quantities; and a therapeutic agent of bead-type chondrocyte without a scaffold prepared by the above method, which has effectiveness in repairing damage by simply being implanted into damaged cartilage by injection.

BACKGROUND

Because cartilage tissue is avascular tissue and the ratio of cells in the tissue is very low, spontaneous regeneration is very limited. After Brittberg et al.'s report (1994) about autologous articular chondrocyte implantation (ACI) in which autologous articular chondrocytes of patients are isolated and proliferated, and then implanted into cartilage damaged area, ACI has been used for the treatment of articular cartilage damage and successful results have been reported in long-term observation. However, in cases of elderly patients and large-size damage, structural features or constitutions of normal articular cartilage cannot be reproduced. In the limits of conventional ACI (first-generation ACI), the following have been indicated as causes: considerably invasive implantation method in which cells in suspension are fixed at damage site with periosteum as a cover, the decreased viability of cells and non-maintenance of phenotype of chondrocytes, and weak physical strength. To overcome such limits, tissue-engineered cartilages—which are second-generation ACI technique using gel, membrane or three-dimensional scaffold as a cell carrier system—have been developed (Hutmacher et al., 2000; Adkisson et al., 2001; Ochi et al., 2001; and Cancedda et al., 2003).

In the preparation of tissue-engineered cartilages, a scaffold provides chondrocytes with three-dimensional system to maintain phenotype of chondrocytes and promote the production of hyaline cartilaginous extracellular matrix (ECM). In addition, the scaffold carries cells to cartilage-damage site and protects cells from loaded force by providing physical support at the implantation site. At present, scaffolds for tissue engineering have been developed by the use of many synthetic or natural materials. However, in view of clinical application, xenogeneic and allogeneic natural materials may cause immune reaction, and in the case of synthetic materials safety problems may be caused due to the harmful degradation product. Furthermore, when chondrocytes are inoculated to a scaffold, most of them distribute to the outer part of the scaffold, and extracellular matrixes which are synthesized and secreted by chondrocytes form shell at the outer part of the scaffold to hinder diffusion and exchange of nutrients, wastes and gases, resulting in death of interior cells. In some studies, successful tissue-engineered cartilages have been made by the use of scaffold. However, there are still many unresolved problems such as interaction between cells and biomaterials, irregular degradability of biomaterials, biocompatibility, uneven cellular distribution, lack of linkage (bonding) between tissue-engineered cartilage and peripheral cartilage and the like (Sittinger et al., 1996; Grande et al., 1997; Nehrer et al., 1998; Sims et al., 1998; Hutmacher et al., 2000; Ochi et al., 2001; Naumann et al., 2004; Park et al., 2006; and Wolf et al., 2008).

Studies about methods for the preparation of three-dimensional cartilage tissue without the use of scaffold have been continually carried out, but it has been reported that such methods are very limited in direct clinical applications since tissues are formed depending on only cells and ECM synthesis capacity of cells so that it is difficult to prepare tissues suitable for the size of damage where implantation is needed (Adkisson et al., 2001; Grogan et al., 2003; and Marlovits et al., 2003). Because cartilage is avascular tissue, it endures hypoxia and undernutrition well. However, Jain et al. (2005) and Rouwkema et al. (2008) state that because all cells in the body are not distant from blood vessels beyond 100 to 200 μm, when tissues for implantation are prepared at laboratories their size should be determined in view of limited nutrients, and diffusion of wastes and gases. In addition, the shape and depth of damaged cartilage are not uniform (FIG. 1A). Therefore, if three-dimensional cartilages prepared at laboratories are larger than the damaged area, implants should be trimmed in accordance with shapes of damages. On the contrary, if cartilage implants are smaller than the damaged area, implantation should be carried out in the manner of putting the pieces as a mosaic in accordance with shapes of damages. Tissue-engineered cartilages developed up to now are implanted in such a manner, but they cannot be adjusted to the thickness of damage. In such a case, at articular cartilages if implants highly protrude or are dented in comparison with adjacent cartilages, additional damages may be caused to implants or adjacent normal cartilage due to abnormal weight load (FIG. 1B).

Therefore, if small bead-type cartilage tissue is prepared, the death of interior cells—which is caused by the problem of perfusion in the course of culture—does not occur, and damaged areas can be restored regardless of the shape and thickness of cartilage-damaged area by inserting several small bead-type tissues into the damaged area. In addition, implantation can be performed by injecting into the damaged area via small incision or an arthroscope without large incision (FIG. 1C). However, for development as a therapeutic agent, a technique for preparing uniform cartilaginous tissues with repetitive reproducibility is necessary, and a large-scale culture system for preparing considerably large number of cartilaginous tissues is required for using in wide damaged area.

Methods for the preparation of three-dimensional hyaline cartilaginous tissue without the use of scaffold are based on the high-density three-dimensional culture of chondrocytes or cells having chondrogenic potential, and the maintenance of three-dimensional state in high density is the most important factor to express the phenotype of chondrocytes. At the development stage, after aggregation of chondroprogenitor cells chondrogenic differentiation is facilitated by the increase of initial cell-cell and cell-substrate adhesion molecules (Tavella et al., 1997; Stewart et al., 2000; Anderer et al., 2002; and Zhang et al., 2004).

Among methods in which small cartilaginous structures without a scaffold are prepared, first of all a pellet culture is a method in which from the initial step of three-dimensional culture an ultra-high-density culture system of cells is artificially made by the use of cell condensation which is prepared by centrifuging a considerably small number of cells. A pellet-formation procedure is simple and easily reproducible, and cells having chondrogenic potential make cartilaginous tissues by synthesizing and secreting cartilaginous matrix under this system (Zhang et al., 2004). A pellet culture method is the most frequently used method to evaluate chondrogenic potential of stem cells (Pittenger et al., 1999), and is also used for evaluating effects of external factors on chondrocytes (Croucher et al., 2000; Graff et al., 2000; Stewart et al., 2000; and Larson et al., 2002). However, evaluation of applicability of cartilaginous structure prepared by pellet culture as a cell-therapy product has not been carried out since a pellet system is a useful method for preparing high quality cartilaginous tissues but it has been regarded being difficult to apply to regeneration of damaged cartilage for the problem of difficulty in preparing sufficient pellet size. In addition, a general pellet culture uses a method in which cell suspension is added to a tube with a lid (a conical tube, a storage tube, a microcentrifuge tube and the like) and centrifuged, and three-dimensional culture is then carried out so that it can prepare only one pellet per one tube. As a result, it is difficult to apply this method to large-scale culture (FIG. 2A).

As methods for preparing small cartilage structure without a scaffold, there is a method to induce aggregation of cells spontaneously. Moscona et al. (1961) prepared a cell aggregate named as "aggregation pattern" by the use of rotation technique. They reported that when dynamic culture of cells suspended in a culture medium is carried out, a cell aggregate is spontaneously formed via interaction between cells (FIG. 2B). Landry et al. (1985; 1984) operated with cells on a non-adherent plastic substratum to prepare a three-dimensional cell aggregate and named it as "spheroid." Reginato et al. (1994), Stewart et al. (2000), Anderer et al. (2000) and Wolf et al. (2008) induced the formation of spontaneous cell aggregate by culturing chondrocytes in a non-adherent culture dish coated with agarose or hydrogel (FIG. 2C). In such spontaneous spheroid system, cells form a three-dimensional cell aggregate and produce their own extracellular matrix (ECM) which is similar to natural matrix of hyaline cartilage. However, this culture method cannot adjust the number of cells which produce one cell aggregate, and there is a disadvantage of not being standardized as a tissue-engineered/cell therapy product since the size of each cartilaginous tissue and chondrification vary due to the possibility of fusion between formed cartilaginous tissues.

As another method to induce aggregation of cells spontaneously, there is a method uses an adherent culture dish. Imabayashi et al. (2003) placed drops of high-concentration suspension of cells having chondrogenic potential on an adherent culture dish and kept it in a 37° C. incubator. After several hours or days, cells were aggregated, and this aggregate was suspended in culture medium and three-dimensional culture was then carried out in a non-adherent culture dish or dynamic culture condition (FIG. 2D). This method, known as micromass/chondrosphere culture, has an advantage in that the number of cells forming cartilaginous tissue can be adjusted. However, it cannot be guaranteed to stably obtain uniform cartilaginous tissues since the capacity of forming cell aggregate spontaneously is different depending on cell condition. In addition, if cell aggregates are cultured all together before hardening of ECM, fusion between cartilaginous tissues may occur.

To equalize the number of cells forming cell aggregate spontaneously, studies using microwells have been conducted. In the three-dimensional culture of hepatocytes, if the hepatosphere is large, necrosis of internal core may occur. As a result, there is a need to develop three-dimensional culture system capable of preparing large amounts of uniform hepatospheres with a desired size. Fukuta et al. (2006) developed a method like to micromolding techniques as one of such methods. Wong et al. (2011) and Choi et al. (2010) prepared concave micromolds with 300-500 μm diameters based on thin poly-dimethylsiloxane (PDMS) membrane. They reported that when hepatocytes are cultured on plane PDMS surface, or in cylindrical or concave microwells to form spheroids, the size and shape of spheres formed in concave microwells were uniform; their size was perfectly regulated by the diameter of the concave microwells; cells cultured in concave microwells formed spheres more rapidly than those cultured in cylindrical microwells or on planar surfaces; and the spheres formed in concave microwells were easily harvested, which was a great advantage for generating stable spheres (FIG. 2E). After commercialization of molds, micro-tissue preparation methods using micromolds have been evaluated in various cells. However, because they are also methods to induce spontaneous cellular aggregation, it cannot be guaranteed that they stably obtain uniform cartilaginous tissues. In addition, because the size of prepared cell aggregates is too small, physical strength is weak and handling is difficult, so there is a limit in it being used as a therapeutic agent of three-dimensional chondrocyte.

As such, methods known up to now as those for preparing three-dimensional cartilage tissue without the use of scaffold have problems such that sufficient pellet size is not formed, it is not suitable for large-scale preparation, uniform cartilage tissue with repetitive reproducibility is not formed, the size of formed cell aggregate is too small, and strength is low. Therefore, such methods are inappropriate for the preparation of a therapeutic agent of bead-type chondrocyte without a scaffold

DISCLOSURE OF INVENTION

Technical Problem

Accordingly, the present invention is intended to provide a method for preparing three-dimensional cartilage tissue without using a scaffold, specifically a novel method which is suitable for the preparation of bead-type cartilage tissue. The technical problem of the present invention is the provision of a method for preparing a therapeutic agent of bead-type chondrocyte which is capable of easily and stably preparing uniform, high-quality cartilage tissues with repetitive reproducibility in large quantities by a simple method using an easily purchasable 96-well deep well plate having V-shaped bottom. In addition, the present inventors confirmed that a therapeutic agent of bead-type chondrocyte without a scaffold prepared by the above method has effectiveness in repairing damage by simply being implanted into cartilage damage by injection in practice. As such, another technical problem of the present invention is the provision of a therapeutic agent of bead-type chondrocyte without a scaffold prepared by the above method.

Technical Solution

To resolve the above object, the present invention provides a method for preparing a therapeutic agent of bead-type chondrocyte without a scaffold which comprises the steps of: a) dispensing chondrocyte and/or cell having chondrogenic potential into a 96-well deep well plate having V-shaped bottom; b) centrifuging the plate; c) three-dimensionally culturing the plate in an incubator; and d) collecting a pellet from each well.

In addition, the present invention provides a therapeutic agent of bead-type chondrocyte without a scaffold prepared by the above method, which has effectiveness in repairing damage by simply being implanted into cartilage damage by injection.

Furthermore, the present invention provides a cartilage-bone bilayer structure for the treatment of osteochondral damage comprising the above therapeutic agent of bead-type chondrocyte; and bone and/or bone graft material Effects The present invention uses a 96-well deep well plate having V-shaped bottom in the preparation of three-dimensional cartilage tissue without a scaffold, thereby being capable of easily and stably preparing uniform, high-quality cartilage tissues with repetitive reproducibility in large quantities; being capable of automation; and being capable of preparing a therapeutic agent of bead-type chondrocyte which has effectiveness in repairing damage by simply being implanted into cartilage damage of patients by injection, as compared with conventional culture methods.

BRIEF DESCRIPTION OF DRAWINGS

The patent or application file contains at least one drawing executed in color. Copies of this patent or patent application publication with color drawings will be provided by the Office upon request and payment of the necessary fee.

BEST MODE

The present invention is described in detail hereinafter.

The method for preparing a therapeutic agent of bead-type chondrocyte of the present invention comprises the following steps:

a) dispensing chondrocyte and/or cell having chondrogenic potential into a 96-well deep well plate having V-shaped bottom;

b) centrifuging the plate;

c) three-dimensionally culturing the plate in an incubator; and d) collecting a pellet from each well.

According to one aspect, the method for preparing a therapeutic agent of bead-type chondrocyte of the present invention may comprise the following steps:

a) dispensing chondrocyte and/or cell having chondrogenic potential into a 96-well deep well plate having V-shaped bottom;

b) centrifuging the plate;

c) three-dimensionally culturing the plate in an incubator;

c-1) exchanging a culture medium; and d) collecting a pellet from each well.

Surprisingly, the present inventors found that uniform, high-quality bead-type cartilage tissue can be easily and stably prepared with repetitive reproducibility in large quantities by a simple method using a commercially available 96-well deep well plate having V-shaped bottom.

The first step of the preparation method according to the present invention is the dispensation of chondrocyte and/or cell having chondrogenic potential into a 96-well deep well plate having V-shaped bottom. A 96-well deep well plate having V-shaped bottom used in the preparation method of the present invention may be any plate which is commercially available, but a plate having well volume of 500 μl or more, which is suitable for accommodating culture medium of 400 μl or more, is preferable. In the following example, a 96-well deep well plate having V-shaped bottom and well volume of 600 μl which is commercially available from Axygen Scientific, Inc. (Corning Life Science, USA) is used, but is not limited thereto.

Figure 8A:
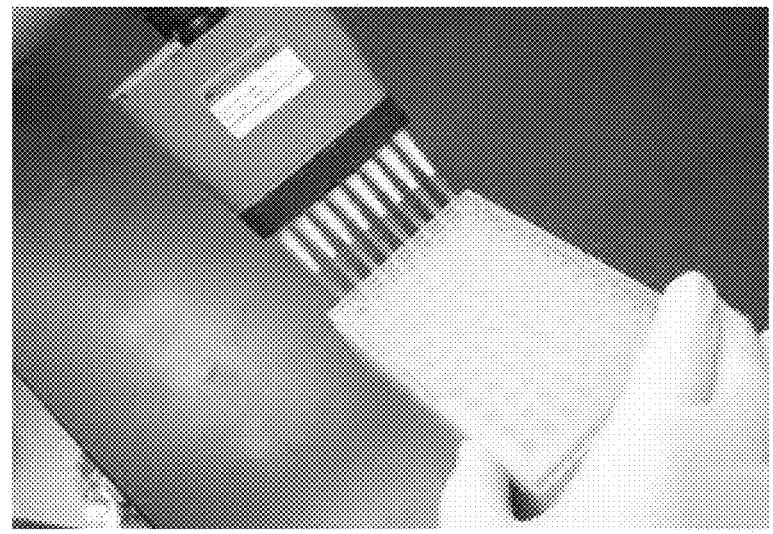
FIGS. 8a and 8b represent an apparatus in which cells can be inoculated into each well and culture media can be exchanged at the same time, and an applicable automation system.
Figure 8B:
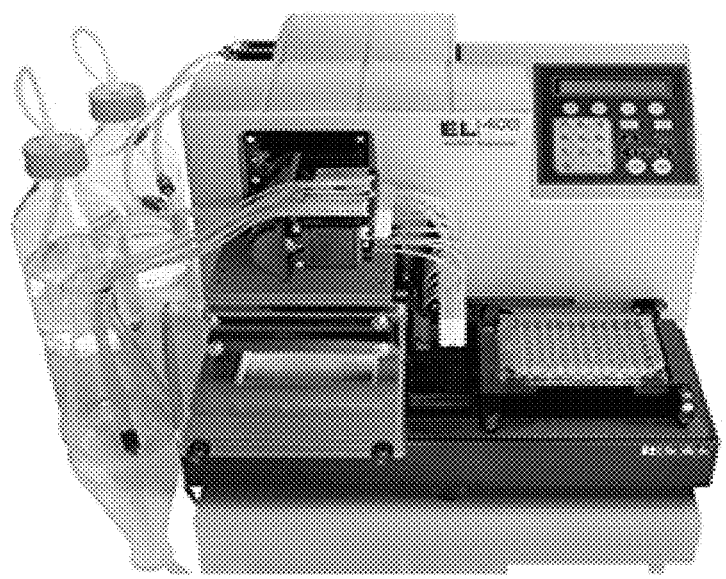

In the preparation method of the present invention, an apparatus for inoculating cells into each well of a 96-well deep well plate having V-shaped bottom at the same time is already commercially available. For example, FIGS. 8a and 8b illustrate an apparatus for inoculating cells into each well and exchanging culture media at the same time, and an applicable automation system. Preferably, it may be carried out by the use of an apparatus selected from the group consisting of a multi-channel pipette, a multi-pipette, a microplate washer and a microplate dispenser.

Chondrocyte or cell having chondrogenic potential used in the present invention is that derived from a mammal. For example, it includes, but is not limited to, human, cattle, pig, horse, dog, goat, rabbit, mouse and the like. Preferably, chondrocyte and/or cell having chondrogenic potential isolated from human, rabbit or goat is (are) used.

In the present invention, the term "chondrocyte" is a concept including chondroblast, which is a cell in which its differentiation is determined to be chondrocyte. The term "cell having chondrogenic potential" refers to a cell which has a capacity of differentiating to chondrocyte under proper culture condition. Preferably, the cell having chondrogenic potential is selected from the group consisting of mesenchymal stem cell, embryonic stem cell and induced pluripotent stem cell, and the mesenchymal stem cell may be adipose-derived, bone marrow-derived, umbilical cord-derived, umbilical cord blood-derived, placenta-derived, synovium-derived, periosteum-derived or perichondrium-derived cell.

The amount of chondrocyte or cell having chondrogenic potential dispensed into a 96-well deep well plate having V-shaped bottom is in the range of $0.1 \times 10^5$ cells/well to $5.0 \times 10^5$ cells/well, preferably $0.5 \times 10^5$ cells/well to $2.0 \times 10^5$ cells/well. At this time, the amount of culture medium is in the range of 300 μl/well to 2,000 μl/well, preferably 400 μl/well to 600 μl/well. In the following example, cells with $0.5 \times 10^5$ cells/400 μl/well, $1.0 \times 10^5$ cells/400 μl/well or $2.0 \times 10^5$ cells/400 μl/well were dispensed, respectively, and then evaluated for 28 days. As a result, all showed satisfactory results in the formation of bead-type pellets. However, the size of pellets did not continuously increase in direct proportion to the number of inoculated cells. Specifically, $2.0 \times 10^5$ cells/400 μl/well is double the number of inoculated cells as compared with $1.0 \times 10^5$ cells/400 μl/well, but the size of formed pellet did not make much of a difference to a certain time (e.g., on the $28^{th}$ day) and the two-dimensional area was only about 1.1 to 1.3 times.

The second step of the preparation method according to the present invention is the centrifugation of the 96-well deep well plate wherein cells are dispensed. The centrifugation may be carried out at 200 to 3,000 rpm for 5 to 15 minutes, preferably at 500 to 2,000 rpm for 5 to 10 minutes. Concrete examples of centrifugation condition may be at 500 rpm for 15 minutes, at 1,000 rpm for 10 minutes, at 1,000 rpm for 5 minutes, at 1,500 rpm for 5 minutes, or at 2,000 rpm for 5 minutes, but are not limited thereto. Most preferably, the centrifugation is carried out at 1,200 rpm for 5 minutes.

The third step of the preparation method according to the present invention is the three-dimensional culture of the centrifuged 96-well deep well plate in an incubator. For three-dimensional culture in an incubator, the condition conventionally used in this technical field may be used at it is. In one embodiment, the three-dimensional culture of cells is carried out in a 37° C., 5% $CO_2$ incubator. There is no limitation in the kind of culture medium, but the use of serum-free culture medium is preferable. In one embodiment, the culture medium is a medium for chondrogenic differentiation.

In the present invention, the three-dimensional culture is carried out for at least 3 more days, preferably 3 to 30 days, and most preferably 3 to 20 days. If the culture is carried out for less than 3 days, the sufficient size of pellet may not be obtained, and pellets may show properties of not firmly aggregating and releasing. In addition, if the culture is carried out for more than 30 days, it may be undesirable to obtain high-quality cartilage tissue due to excessive occurrence of dead cells and chondrocytus hypertrophicus.

According to one aspect, the preparation method of the present invention may further comprise the step of exchanging a culture medium. Preferably, the three-dimensional culture of cells may be carried out with exchanging culture media at an interval of 3 or 4 days. In such a medium exchange, the apparatuses used in inoculating cells into each well of a 96-well deep well plate having V-shaped bottom at the same time at the first step may be used, and these apparatuses are already commercially available. FIGS. 8a and 8b illustrate an apparatus for exchanging culture media and an applicable automation system. Preferably, it may be carried out by the use of apparatus selected from the group consisting of a multi-channel pipette, a multi-pipette, a microplate washer and a microplate dispenser.

Figure 8C:
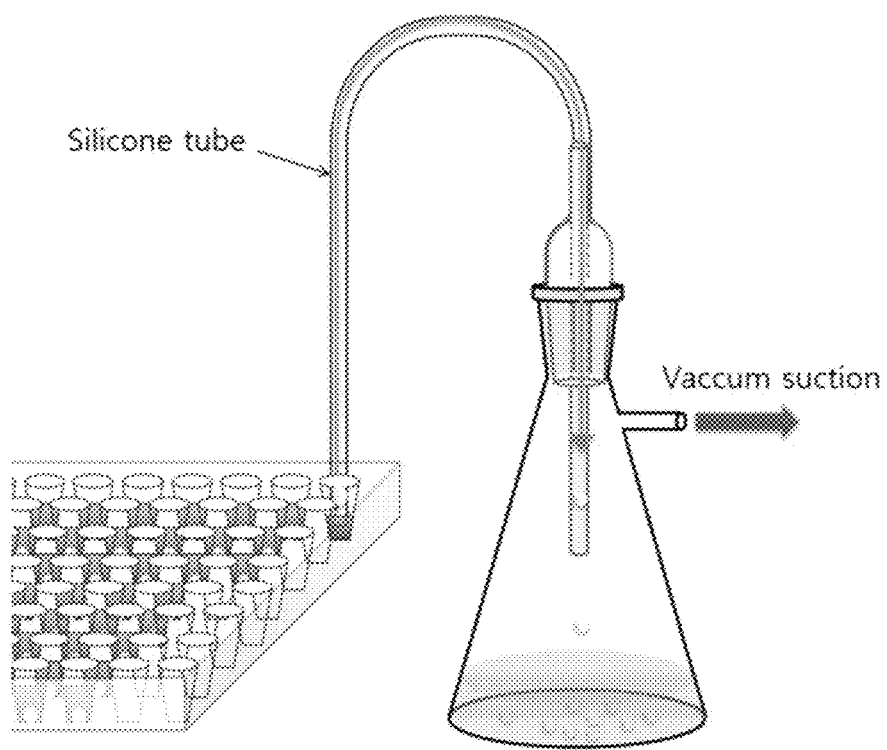
FIG. 8c is a schematic diagram of portable pellet collection apparatus.

After completion of culture, pellets are collected in accordance with the final step of the preparation method according to the present invention. There is no limitation in collecting pellets, and a method using a vacuum suction pump conventionally used in this technical field may be used. As such example, the portable pellet-collection apparatus illustrated in FIG. 8c may be used.

As confirmed by the following examples, the structures prepared according to the preparation method of the present invention show properties of smooth surface, whiteness and translucence as like hyaline cartilage from the $3^{rd}$ day of three-dimensional culture.

With respect to the size, in the case of $0.5 \times 10^5$ cells/well the diameter was about 0.5 mm on the $3^{rd}$ day, and the size was slowly increased according to the increase of culture time so that the diameter was about 1 mm on the $28^{th}$ day. In the case of $1.0 \times 10^5$ cells/well, a sphere having the diameter of about 1 mm was formed on the $3^{rd}$ day, and the size was slowly increased according to the increase of culture time so that the diameter was about 1.5 mm on the $28^{th}$ day. Through overall three-dimensional culture, $1.0 \times 10^5$ cells/well formed the sphere having about double the size of sphere as compared with $0.5 \times 10^5$ cells/well. However, in the case of three-dimensional structure prepared from $2.0 \times 10^5$ cells/well, a sphere having the diameter of about 1 mm was formed on the $3^{rd}$ day, and the size was slowly increased according to the increase of culture time so that the diameter was about 1.5 mm on the $28^{th}$ day. As such, there was no difference in size as compared with the three-dimensional structure prepared from $1.0 \times 10^5$ cells/well.

With respect to the two-dimensional area measured with microscope photographs, $0.5 \times 10^5$ cells/well was about 0.28 mm$^2$ on the $3^{rd}$ day of three-dimensional culture. On the $7^{th}$, $14^{th}$, $21^{st}$ and $28^{th}$ days, the two-dimensional area was 0.71, 0.92, 1.25 and 1.12 mm$^2$, respectively, which were slowly increased according to the increase of culture time, but on the $28^{th}$ day it was decreased by about 10% as compared with the $21^{st}$ day. In $1.0 \times 10^5$ cells/well, the two-dimensional area was about 1.06 mm$^2$ on the $3^{rd}$ day of three-dimensional culture. On the $7^{th}$, $14^{th}$, $21^{st}$ and $28^{th}$ days, the two-dimensional area was 1.43, 1.66, 1.91 and 1.74 mm$^2$, respectively, which were slowly increased according to the increase of culture time, but on the $28^{th}$ day it was decreased by about 10% as compared with that of the $21^{st}$ day. In $1.0 \times 10^5$ cells/well, the structure having about 2 to 3.8 times the size was formed as compared with that prepared from $0.5 \times 10^5$ cells/well until the $14^{th}$ day of the culture, since then the size was about 1.5 times. In $2.0 \times 10^5$ cells/well, on the $3^{rd}$, $7^{th}$, $14^{th}$, $21^{st}$ and $28^{th}$ days, the two-dimensional area was 1.25, 1.68, 2.01, 2.13 and 2.33 mm$^2$, respectively, which were slowly increased according to the increase of culture time. The number of inoculated cells was double as compared with $1.0 \times 10^5$ cells/well, but the size of the structure was 1.1 to 1.3 times.

In addition, as a result of dispensing rabbit costal chondrocytes with $1.0 \times 10^5$ cells/400 μl/well and carrying out pellet culture for 10 days, semitranslucent bead-type three-dimensional structures having white and smooth surface with the naked eye and 1.0 to 1.5 mm of diameter were observed. Their plane sizes were in the range of 1.6 mm$^2 \pm 20\%$, and the formation of uniform pellets in each well of a 96-well deep well plate irrespective of cell-supplying subjects was observed.

Furthermore, as a result of dispensing human costal chondrocytes with $1.0 \times 10^5$ cells/400 μl/well and carrying out pellet culture for 10 days, semitranslucent, small bead-type three-dimensional structures having white and smooth surface with the naked eye and 1.0 to 1.5 mm of diameter were obtained. As a result of measuring the size of 30 beads per lot, it can be known that the size is uniform.

Meanwhile, the present invention is directed to a therapeutic agent of bead-type chondrocyte without a scaffold prepared by the above method. The therapeutic agent of bead-type chondrocyte of the present invention comprises a pellet prepared by the above method as an active ingredient, and may further comprise one or more pharmaceutically acceptable carriers known in the art, if necessary. Damaged areas can be restored regardless of the shape and thickness of the area of damaged cartilage by inserting the therapeutic agent of bead-type chondrocyte of the present invention into the damaged area, and implantation can be performed by injecting it into the damaged area via small incision or an arthroscope without large incision. Therefore, the therapeutic agent of bead-type chondrocyte of the present invention shows effectiveness to repair damage by simply being implanted into cartilage damage by injection.

In one embodiment, before the injection of therapeutic agent of bead-type chondrocyte according to the present invention into the damaged area of cartilage, a fibrin glue or autologous platelet rich plasma (PRP) obtained by the centrifugation of the blood may be used for adhesion between these pellets.

Examples of the organic solvent (F) included in a photo-curable paint composition of the present invention may include inert organic solvents usually used in the paint composition, for example, alcohols such as methoxy propanol, isopropyl alcohol, etc., ketones such as acetone, etc., acetates such as ethylacetate, etc., aromatic compounds such as toluene, etc., and combinations thereof, and may preferably include as single solvents alcohols such as methoxy propanol, isopropyl alcohol, etc.

In addition, the present invention is directed to a cartilage-bone bilayer structure for the treatment of osteochondral damage comprising the above therapeutic agent of bead-type chondrocyte; and bone and/or bone graft material. Hydroxyapatite is mineral material which is comprised in calcified tissues in the body such as teeth or bone, and has the highest crystallizability among calcium phosphate compounds so that the degradation rate is slow as much. However, because hydroxyapatite exists in the body, biocompatibility is high, and it has been known that hydroxyapatite shows the best bone-regeneration effect among bone graft materials. Therefore, a preferable bone graft material is hydroxyapatite-tricalcium phosphate (HA-TCP), but is not limited thereto. In one embodiment, a cartilage-bone bilayer structure in the form of a sandwich for evaluating integration between bone and cartilage which is regenerated—in which a cartilage part is prepared by mixing several pellets and fibrin glue, and a bone part prepared by mixing HA-TCP and bone marrow-derived mesenchymal stem cells (BMSCs) is placed below the cartilage part—may be prepared. Such a cartilage-bone bilayer structure is specifically suitable for restoration of osteochondral damage.

Hereinafter, the present invention is explained in more detail with the following examples. However, the following examples are only intended to facilitate understanding of the present invention, and the protection scope of the present invention is not limited thereto.

EXAMPLES

Examples 1

Isolation and Proliferation of Chondrocytes

Costal cartilage tissues were washed with phosphate-buffered saline (PBS) containing antibiotics 3-5 times to remove blood and contaminants. The cartilages were minced into 1-2 mm$^3$, and extracellular matrix was then digested by the treatment of 0.5% pronase and 0.2% type II collagenase to isolate cells. After the inoculation of isolated cells into culture dishes at a cell density of $2-4 \times 10^4$ cells/cm$^2$, a culture medium for cell proliferation (mesenchymal stem cell growth medium [MSCGM] containing 1 ng/ml of FGF-2) was added thereto, and the cells were then cultured until being confluent in a 37° C., 5% $CO_2$ incubator. Cells detached from the culture dishes with a trypsin-EDTA solution were inoculated into culture dishes at a cell density of $1-2 \times 10^4$ cells/cm$^2$, and cultured to passages 6 to 8.

Three-dimensional Pellet Culture of Chondrocytes at Various Kinds of 96-well Plates or 96-well Deep well Plates Proliferation completed cells at passages 6 to 8 were suspended in a culture medium for chondrogenic differentiation (DMEM, 50 μg/mL of gentamicin, 10 ng/mL of TGF-beta 3, 1% ITS+3, 100 nM dexamethasone, 50 μg/mL of ascorbic acid and 40 μg/mL of L-proline), and the suspension was dispensed into (1) a 96-well plate (300 μl well volume) having V-shaped bottom with $1.0 \times 10^5$ cells/200 μl/well, (2) a 96-well plate (300 μl well volume) having flat bottom with $1.0 \times 10^5$ cells/200 μl/well, (3) a 96-well deep well plate (600 μl well volume) having concave bottom with 1.0×10⁵ cells/400 μl/well, and (4) a 96-well deep well plate (600 μl well volume) having V-shaped bottom with 1.0×10⁵ cells/400 μl/well. The plates were centrifuged at 1,200 rpm for 5 minutes, and then three-dimensionally cultured in a 37° C., 5% $CO_2$ incubator for 28 days with exchanging culture media at an interval of 3 or 4 days.

Results

Figure 1:
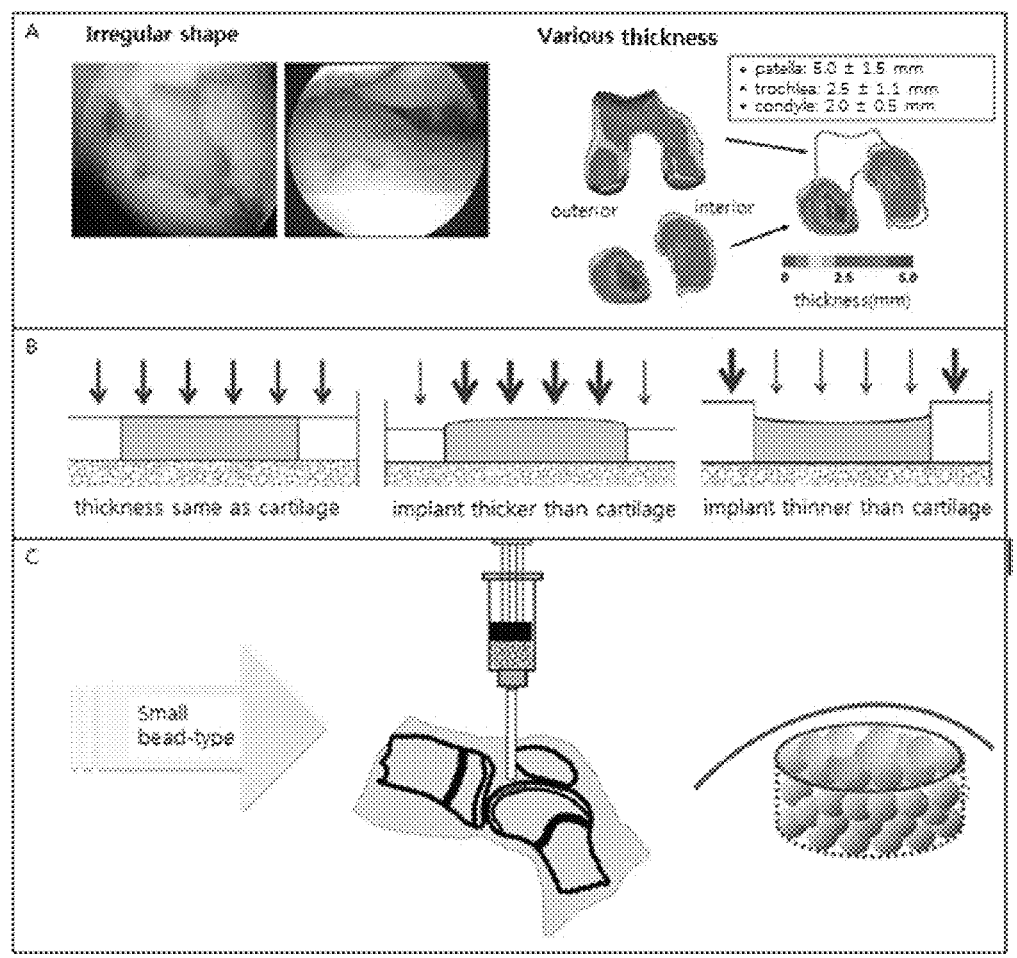
FIG. 1 is a drawing which schematically shows the necessity of bead-type cartilage tissue implant. A shows irregular shape of cartilage damage and various thickness of knee cartilage. B shows phenomenon that in the case of single standard (thickness) of implant it is implanted in the form of protruding or being dented from the face of cartilage depending on the thickness of the cartilage, which results in imposing an abnormal weight load on the implant or adjacent normal cartilage. C shows that small bead-type implant can be implanted irrespective of the shape/thickness of cartilage damage by injection.
Figure 2:
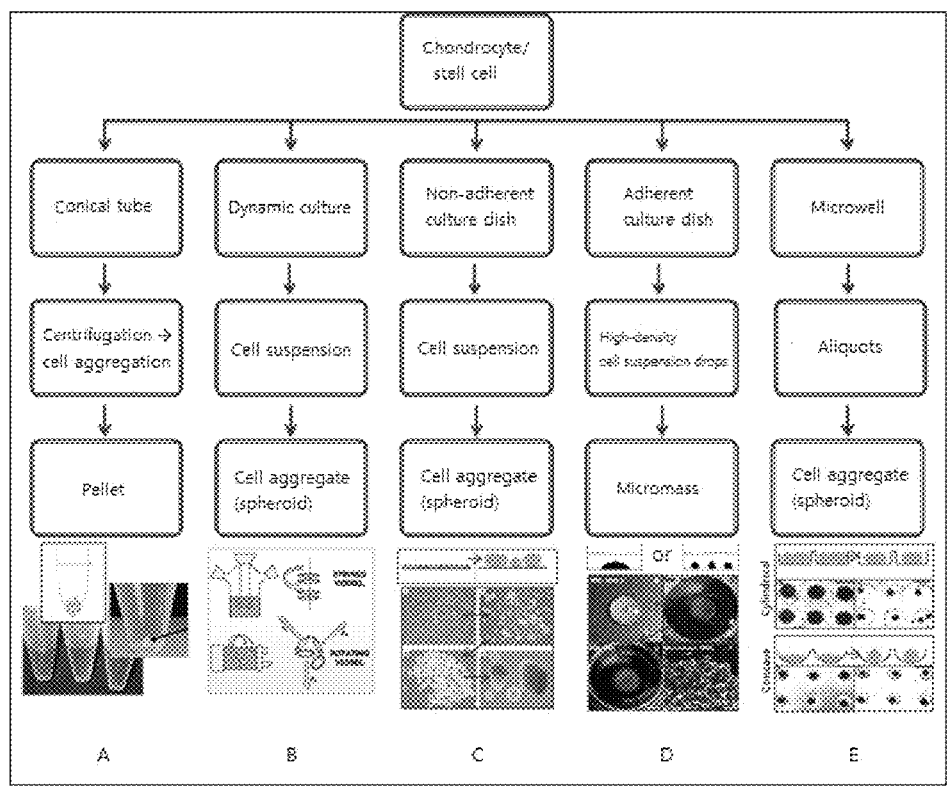
FIG. 2 is a drawing which schematically shows various methods for preparing three-dimensional cartilage tissues without a scaffold from chondrocytes or stem cells.
Figure 3A:
FIG. 3a is a photograph showing the difference of well depth (height) between a 96-well deep well plate and a typical 96-well plate.
Figure 3B:
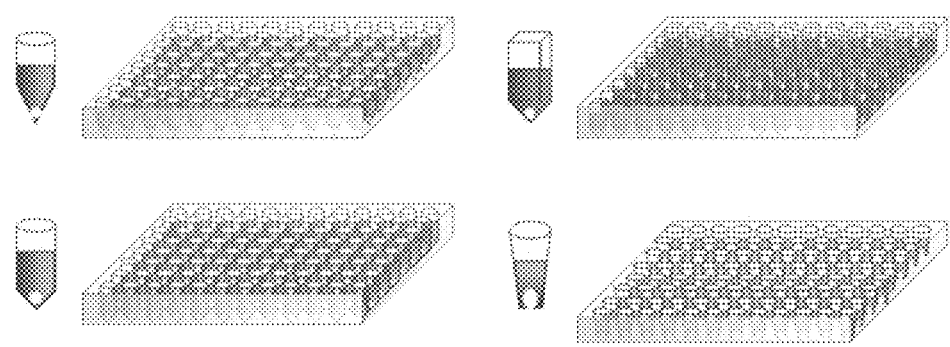
FIG. 3b is a schematic diagram showing 96-well deep well plates having various shape of V-shaped bottom and the formation of bead-type cartilage tissue (pellet) in each well.
Figure 4A:
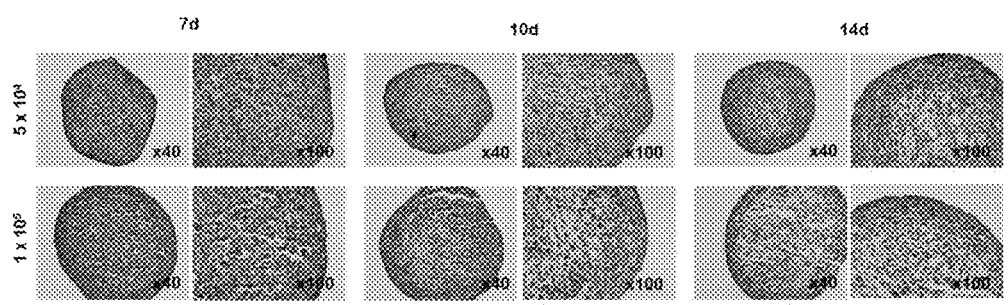
FIG. 4a is a photograph showing the result of histological staining (GAG) of chondrocytes which were three-dimensional pellet cultured in a 96-well plate (300 μl well volume) having V-shaped bottom.
Figure 4B:
FIG. 4b is a photograph of chondrocytes which were three-dimensional pellet cultured in a 96-well plate (300 μl well volume) having flat bottom.
Figure 4B:
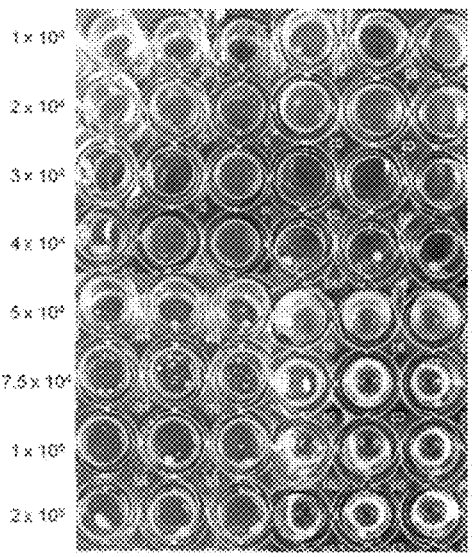
Figure 4C:
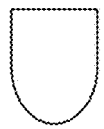
FIG. 4c is a photograph of chondrocytes which were three-dimensional pellet cultured in a 96-well deep well plate having concave bottom.
Figure 4C:
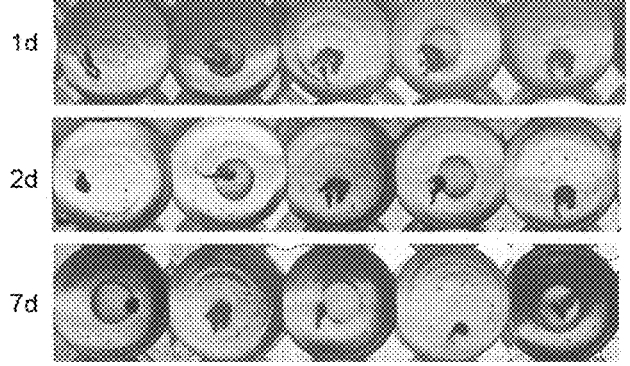
Figure 4D:
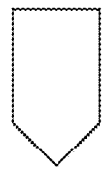
FIG. 4d is a photograph of chondrocytes which were three-dimensional pellet cultured in a 96-well deep well plate having V-shaped bottom.
Figure 4D:
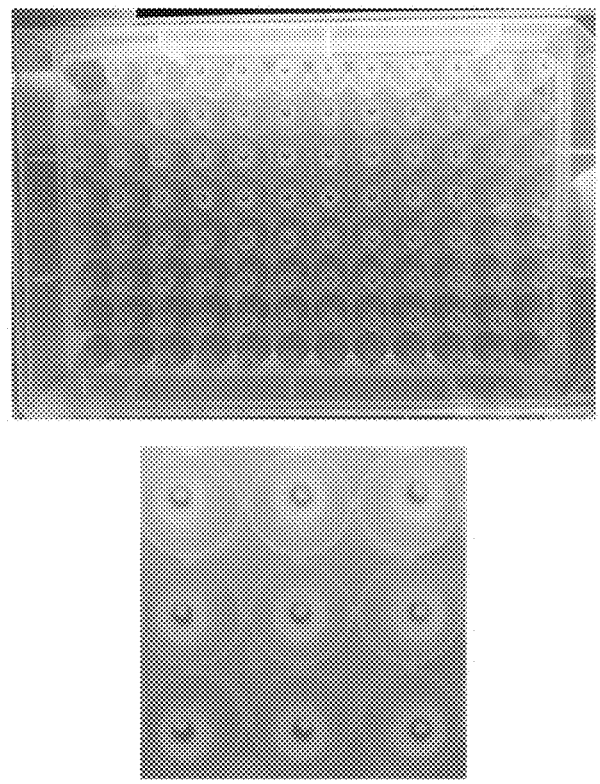

In the 96-well plate (300 μl well volume) having V-shaped bottom, spheres were well formed, but as a result of evaluation according to Safranin O GAG staining method of (4) histological properties and immunostaining of the following Example 2, it can be known that chondrogenic differentiation did not occur on the basis of cell morphology and expression of cartilaginous matrix (FIG. 4a). In the three-dimensional culture using the 96-well plate (300 μl well volume) having flat bottom, spheres having complete shape were not stably formed (FIG. 4b). In the three-dimensional culture using the 96-well deep well plate (600 μl well volume), when the bottom shape of the well is concave, spheres having complete shape were not stably formed in spite of the step of centrifugation (FIG. 4c). However, when the bottom shape of the well is V-shaped, spheres having stably uniform size were observed one per well, and the structure which is firm to some extent was formed on the $3^{rd}$ day of three-dimensional culture (FIG. 4d).

Example 2

Preparation of Bead-type Three-dimensional Cartilage Tissue

Rabbit chondrocytes cultured in a culture medium for cell proliferation to passages 6 to 8 were pellet cultured in a 96-well deep well plate having V-shaped bottom with 0.5×10⁵ cells/400 μl/well, 1.0×10⁵ cells/400 μl/well or 2.0×10⁵ cells/400 μl/well and evaluated for 28 days.

Evaluation Methods for Properties of Bead-type Three-dimensional Cartilage Tissue (1) Appearance and Size In the course of three-dimensional culture, pellets were collected from each well and their properties were evaluated. First of all, appearance was evaluated with the naked eye, and a pellet was mounted on a slide glass and a photograph was taken with a digital camera installed on a microscope with 40× magnifications to measure the area.

(2) DNA Amount

To measure the DNA amount in pellets, 125 μg/mL of papain was added to pellets and homogenized. After overnight treatment at 65° C., the prepared sample was mixed with Hoechst 33258 dye of DNA Quantitation kit (Bio-Rad Laboratories), and absorbance was then measured. Calf thymus DNA (20 ng-10 μg) was used as a standard for quantitative analysis.

(3) Glycosaminoglycan (GAG) Amount

To measure the GAG amount in pellets, pellets were treated with a papain solution (125 μg/mL) at 65° C. overnight to extract GAG ingredient. After centrifugation, supernatant was taken to prepare a test sample. Blyscan dye reagent (Biocolor, UK) was added thereto for the binding reaction of sulfated GAG and dye, and supernatant was then removed by centrifugation. Remaining GAG-dye lump was dissolved in a dye dissociation reagent, and absorbance at 656 nm was then measured. The measured absorbance was quantified on the basis of a standard (chondroitin sulfate, 1.0-5.0 μg).

(4) Histological Properties and Immunostaining

For histological evaluation, pellets were fixed with formalin, and dehydration and paraffin-embedding steps were carried out. The prepared specimen was sectioned at the thickness of 4 to 6 μm with a microtome. After nuclear staining with hematoxylin, GAG was stained by the use of Safranin O staining agent. As a counterstaining, Fast Green was used, and GAG expression and morphological evaluation of cells were carried out.

To evaluate properties of cartilage in the course of three-dimensional culture, the ultrathin section of the pellet was permeabilized with 0.2% triton X-100; treated with hyaluronidase; anti-type I collagen antibody, anti-type II collagen antibody or anti-type X collagen antibody was applied thereto; and then treated with a secondary antibody and streptavidin-peroxidase. Color development was induced with DAB, and Fast Red was used for nuclear staining.

For fluorescent staining, the whole pellet or the ultrathin section of the pellet was permeabilized with 0.2% triton X-100 and treated with 20% normal goat serum to prevent nonspecific reaction. Anti-aggrecan antibody or anti-type II collagen antibody was used as a primary antibody, and an FITC-tagged secondary antibody was used. In the case of the ultrathin section, nuclear staining was carried out with DAPI. The prepared sample was observed with a fluorescent microscope (Olympus Optical Co., Japan).

(5) Apoptosis

To evaluate cell apoptosis in pellets in the course of three-dimensional culture, TUNEL assay (Roche, Germany) was carried out with sections of 4 μm thickness, nuclear was stained with DAPI, and the presence of apoptotic cells was evaluated with a fluorescent microscope.

(6) Collagen Amount

To measure the collagen amount in pellets, pellets were treated with pepsin solution to extract collagen ingredient, a dye solution of Sircol kit (Biocolor) was added to this sample solution, the reaction was carried out with shaking at room temperature, and then the resultant was centrifuged to precipitate dye-binding collagen. After complete removal of supernatant, the precipitate was dissolved in 1N NaOH solution and absorbance at 540 nm was measured. After obtaining a standard curve (0-50 μg), the content of collagen was quantified on the basis of the absorbance measured by the above method.

For quantitative measurement of collagen pro-C-peptide newly synthesized in pellets, Procollagen Type I C-peptide (PIP) EIA kit (Takara Bio Inc., Japan) was used. Pellets were treated with pepsin solution to extract collagen ingredient, and the remaining steps were carried out according to the manufacturer's instruction. The measured peptide amount was quantified on the basis of standard curve within the range of 0-640 ng PIP/mL.

(7) Gene Expression Properties

To evaluate gene expression of cells, reverse transcription of RNA extracted from pellets was carried out to synthesize cDNA. The PCR of the synthesized cDNA was carried out with primers recited in the following Table 1. Electrophoresis of the PCR products was carried out on agarose gel containing ethidium bromide (EtBr), and evaluation was carried out by identifying bands corresponding to the size of each amplified product.

TABLE 1

| | Gene | Product size (bp) | Primer (forward and reverse) |
|---|---|---|---|
| Human | Type II collagen (NM_001844) | 257 | GAC AAT CTG GCT CCC AAC<br>ACA GTC TTG CCC CAC TTA C |
| | Type IX collagen (NM_001851) | 175 | CAG GAA GAG GTC CCA AC<br>GCT GGC TCA CAG AAA CC |
| | Aggrecan (NM_013227) | 157 | GTC TCA CTG CCC AAC TAC<br>GGA ACA CGA TGC CTT TCA C |
| | SOX 9 (NM_000346) | 118 | GAG CAG ACG CAC ATC TC<br>CCT GGG ATT GCC CCG A |
| | Type I collagen (NM_000088) | 251 | GAG AGC ATG ACC GAT GG<br>GTG ACG CTG TAG GTG AA |
| | Type X collagen (NM_000493) | 139 | CCA GCA CGC AGA ATC C<br>GTG TTG GGT AGT GGG C |
| | GAPDH (NM_002046) | 123 | TGG TAT CGT GGA AGG ACT CA<br>GCA GGG ATG ATG TTC TGG A |
| Rabbit | Type II collagen (S83370) | 193 | AGA GAC CTG AAC TGG GCA GA<br>TGA CAC GGA GTA GCA CCA TC |
| | GAPDH (L23961) | 202 | AGG TCA TCC ACG ACC ACT TC<br>GTG AGT TTC CCG TTC AGC TC |

Results (1) Appearance and Size

Figure 5A:
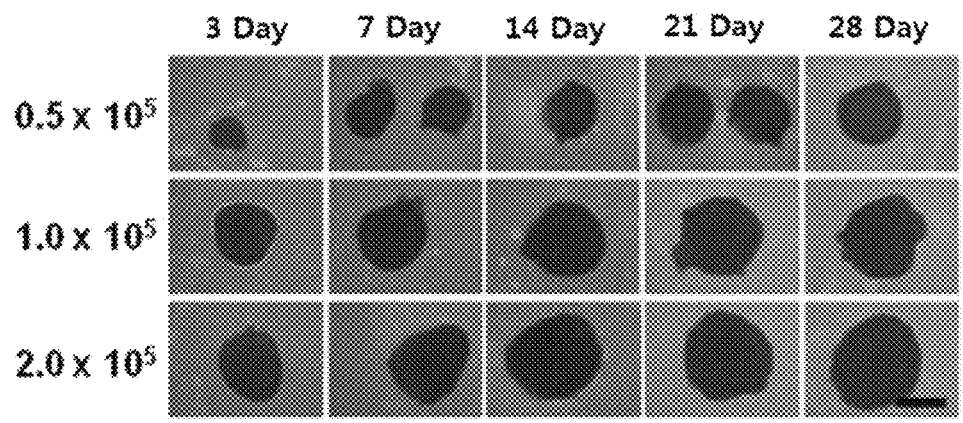
FIGS. 5a to 5h are results of evaluating properties according to initial inoculation cell number and culture time initial inoculation cell number and properties according to incubation time of bead-type cartilage tissue (pellet) which was prepared by three-dimensional pellet culturing rabbit chondrocytes in a 96-well deep well plate having V-shaped bottom.
Figure 5B:
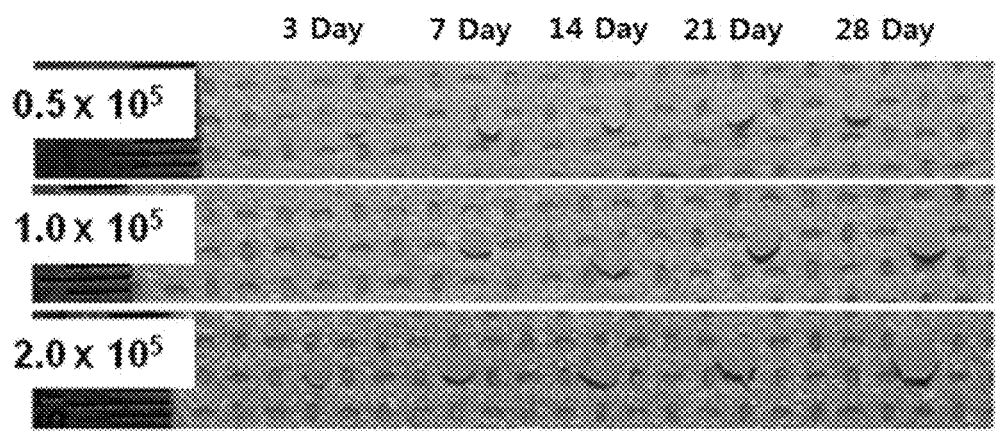

The prepared structure shows properties of smooth surface, whiteness and translucence as like hyaline cartilage from the $3^{rd}$ day of three-dimensional culture. With respect to the size, in the case of $0.5 \times 10^5$ cells/well the diameter was about 0.5 mm on the $3^{rd}$ day, and the size was slowly increased according to the increase of culture time so that the diameter was about 1 mm on the $28^{th}$ day. In the case of $1.0 \times 10^5$ cells/well, the sphere having the diameter of about 1 mm was formed on the $3^{rd}$ day, and the size was slowly increased according to the increase of culture time so that the diameter was about 1.5 mm on the $28^{th}$ day. Through overall three-dimensional culture, $1.0 \times 10^5$ cells/well formed the sphere having about double the size of sphere as compared with $0.5 \times 10^5$ cells/well. However, in the case of three-dimensional structure prepared from $2.0 \times 10^5$ cells/well, the sphere having the diameter of about 1 mm was formed on the $3^{rd}$ day, and the size was slowly increased according to the increase of culture time so that the diameter was about 1.5 mm on the $28^{th}$ day. As such, there was no difference in size as compared with the three-dimensional structure prepared from $1.0 \times 10^5$ cells/well (FIGS. 5a and 5b).

Figure 5C:
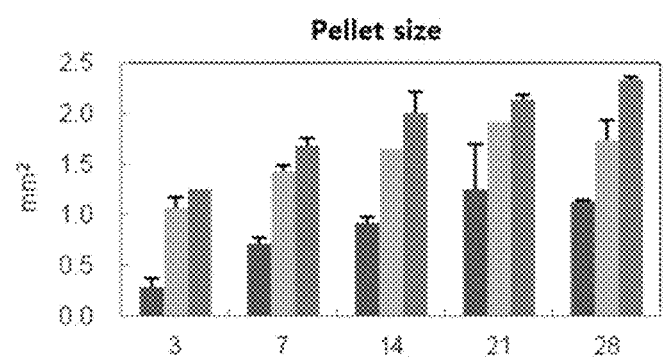

With respect to the two-dimensional area of three-dimensional structure without a scaffold formed from chondrocytes during three-dimensional culture of 28 days which was measured with microscope photographs, $0.5 \times 10^5$ cells/well was about 0.28 mm$^2$ on the $3^{rd}$ day of three-dimensional culture. On the $7^{th}$, $14^{th}$, $21^{st}$ and $28^{th}$ days, the two-dimensional area was 0.71, 0.92, 1.25 and 1.12 mm$^2$, respectively, which was slowly increased according to the increase of culture time, but on the $28^{th}$ day it was decreased by about 10% as compared with the $21^{st}$ day. In $1.0 \times 10^5$ cells/well, the two-dimensional area was about 1.06 mm$^2$ on the $3^{rd}$ day of three-dimensional culture. On the $7^{th}$, $14^{th}$, $21^{st}$ and $28^{th}$ days, the two-dimensional area was 1.43, 1.66, 1.91 and 1.74 mm$^2$, respectively, which was slowly increased according to the increase of culture time, but on the $28^{th}$ day it was decreased by about 10% as compared with that of the $21^{st}$ day. In $1.0 \times 10^5$ cells/well, the structure having about 2 to 3.8 times the size was formed as compared with that prepared from $0.5 \times 10^5$ cells/well until the $14^{th}$ day of the culture, and after that the size was about 1.5 times. In $2.0 \times 10^5$ cells/well, on the $3^{rd}$, $7^{th}$, $14^{th}$, $21^{st}$ and $28^{th}$ days, the two-dimensional area was 1.25, 1.68, 2.01, 2.13 and 2.33 mm$^2$, respectively, which was slowly increased according to the increase of culture time. The number of inoculated cells was double as compared with $1.0 \times 10^5$ cells/well, but the size of the structure was 1.1 to 1.3 times (FIG. 5c).

(2) DNA Amount

Figure 5D:
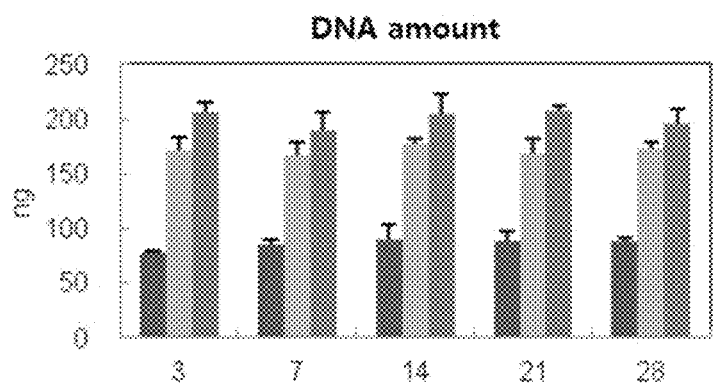

As a result of evaluating the number of cells in pellets during three-dimensional culture by means of DNA amount, $0.5 \times 10^5$ cells/well was about 80 ng, $1.0 \times 10^5$ cells/well was about 170 ng, and $2.0 \times 10^5$ cells/well was about 200 ng, which were constantly maintained all through the culture period. The number of inoculated cells was 2 times, but the DNA amount was 2 times and 1.2 times, respectively (FIG. 5d).

(3) GAG Amount

Figure 5E:
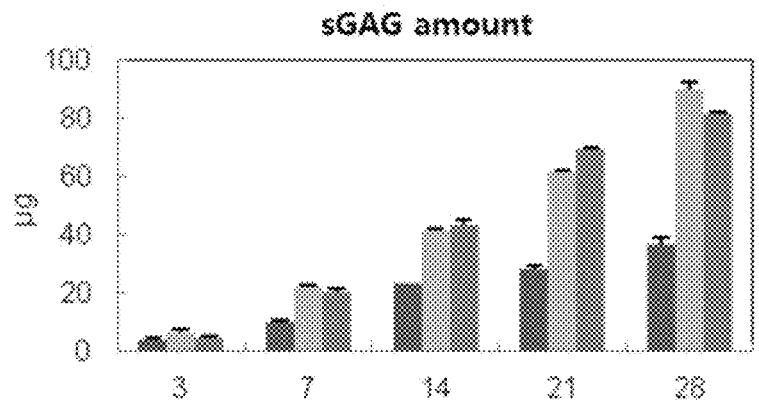

GAG ingredient, which is hyaline cartilage-specific extracellular matrix, was increased according to the increase of culture time. In $1.0 \times 10^5$ cells/well, the GAG amount was about 2 times as compared with $1.0 \times 10^5$ cells/well, but $2.0 \times 10^5$ cells/well showed similar GAG amount as $1.0 \times 10^5$ cells/well (FIG. 5e).

(4) Histological Properties

Figure 5F:
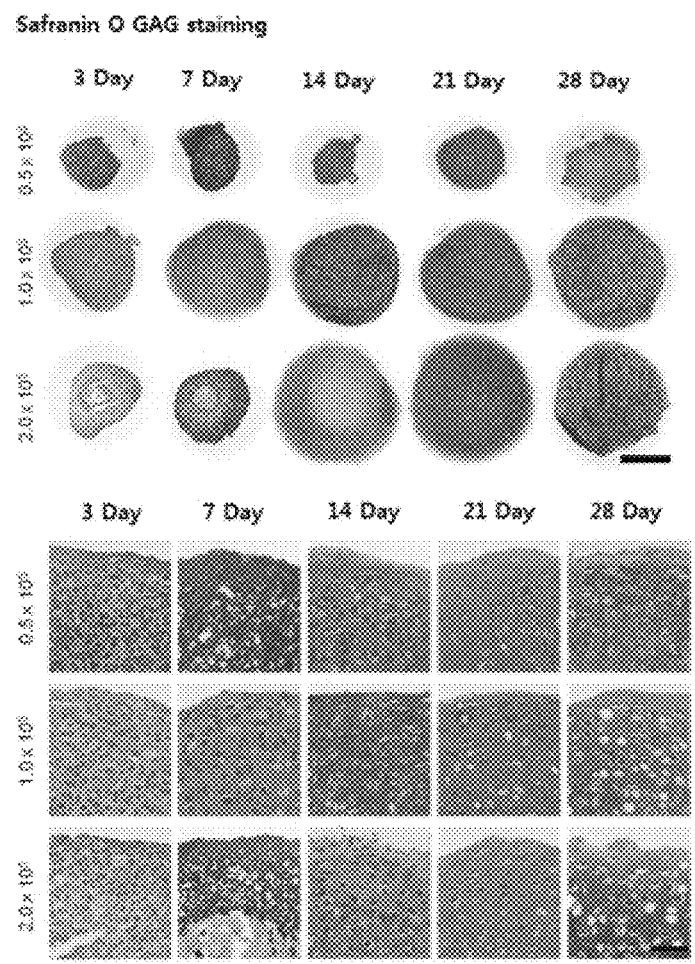

To check whether or not hyaline cartilaginous tissue is formed during three-dimensional culture, the expression of GAG was evaluated by Safranin O staining. As a result, in the case of the three-dimensional structures formed from $0.5 \times 10^5$ cells/well and $1.0 \times 10^5$ cells/well in wells having V-shaped bottom, strong Safranin O staining was observed on entire structures from the $3^{rd}$ day of three-dimensional culture. In the case of $2.0 \times 10^5$ cells/well, the region that is negative to Safranin O was observed at the core of the structure on the $3^{rd}$ and $7^{th}$ days. After that, strong Safranin O staining was observed on the entire structure. On the $3^{rd}$ day of three-dimensional culture, cells were densely populated in the pellet. The shape was round, but the morphology of lacunae was not observed. On the $7^{th}$ day, in the pellet of $1.0 \times 10^5$ cells/well cells existed in distinct lacunae. After the $14^{th}$ day, in all pellets of $0.5 \times 10^5$ cells/well, $1.0 \times 10^5$ cells/well and $2.0 \times 10^5$ cells/well cells enveloped in lacunae were observed, and the morphology of mature hyaline cartilage was shown in process of time (FIG. 5f).

(5) Apoptosis

Figure 5G:
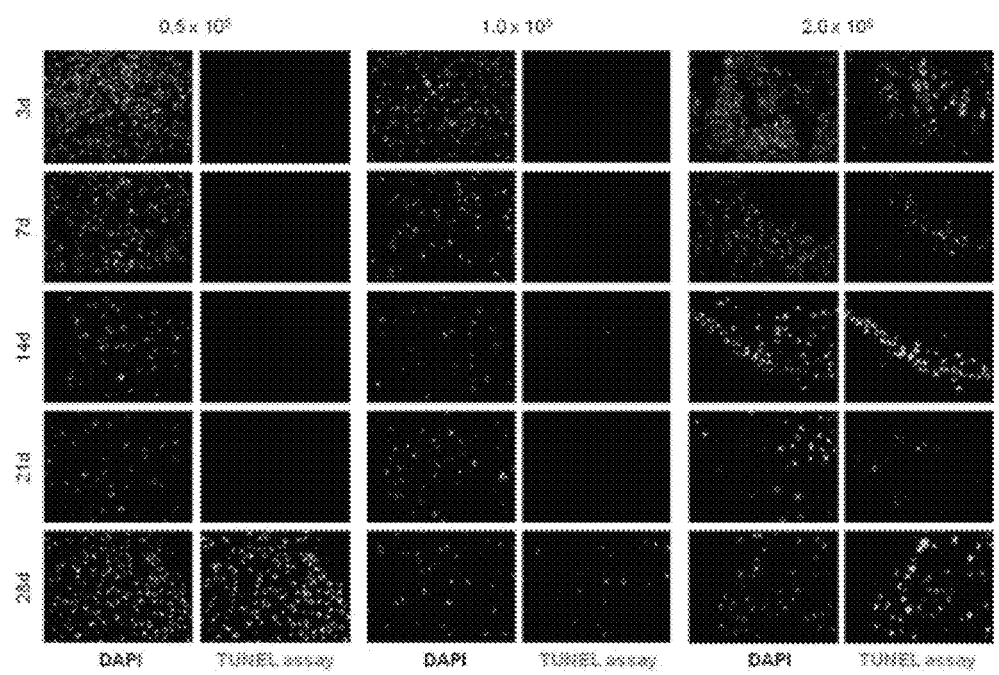

As a result of evaluating apoptosis of cells during three-dimensional culture by TUNEL assay, in the case of $2.0 \times 10^5$ cells/well many apoptotic cells were observed at the core and outside of the pellet from the $3^{rd}$ day to the termination of the culture. In the case of 0.5×10⁵ cells/well and 1.0×10⁵ cells/well, apoptotic cells were observed on the 28$^{th}$ day only (FIG. 5g).

(6) Immunostaining

Figure 5H:
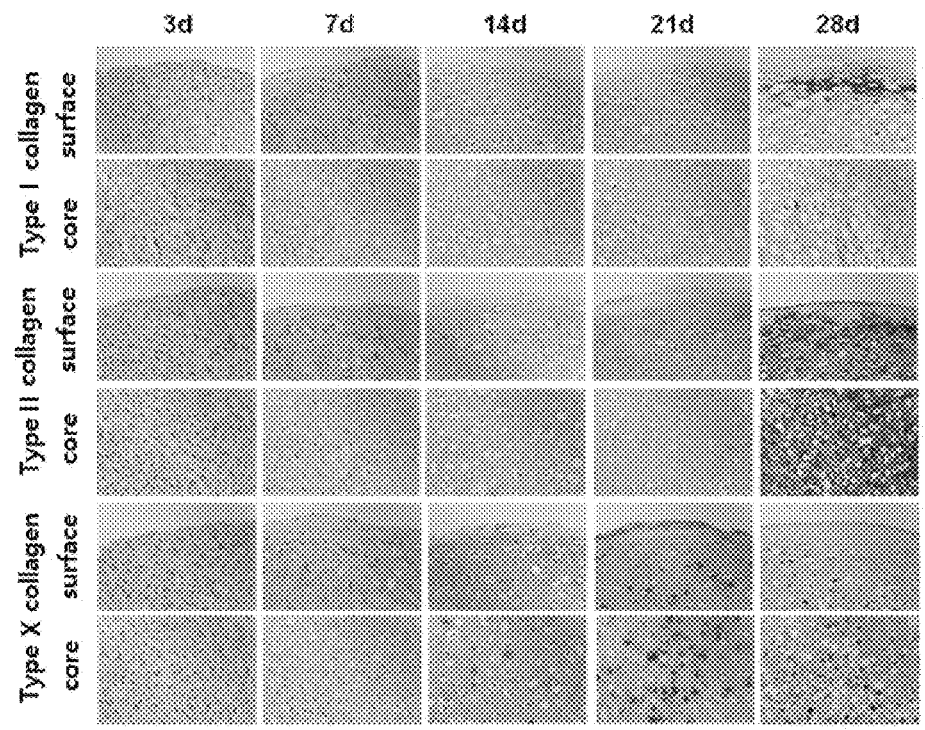

In the pellet of 1.0×10⁵ cells/well, the expression of type I collagen, type II collagen and type X collagen during the three-dimensional culture were evaluated by immunostaining. As a result, type I collagen was expressed outside of the surface only on the 28$^{th}$ day, and type II collagen was strongly stained on the entire pellet except for the outside on the 28$^{th}$ day. In the case of type X collagen, which is a marker of hypertrophic chondrocyte, cells expressing it were observed on the 14$^{th}$ day, and expression ratio was increased in the process of time (FIG. 5h).

Example 3

Rabbit costal chondrocytes cultured in a culture medium for cell proliferation to passages 6 to 8 were suspended in a culture medium for differentiation and dispensed into a 96-well deep well plate having V-shaped bottom with 1.0×10⁵ cells/400 μl/well. The plates were centrifuged at 1,200 rpm for 5 minutes, and then pellet cultured in a 37° C., 5% $CO_2$ incubator for 10 days with exchanging culture media at an interval of 3 or 4 days to prepare a bead-type cartilage tissue without a scaffold for transplanting to articular cartilage damage. After culturing, the bead-type cartilage tissue was collected by the use of portable pellet collection apparatus (FIG. 8c), and properties were evaluated according to the methods described in Example 2.

Figure 6A:
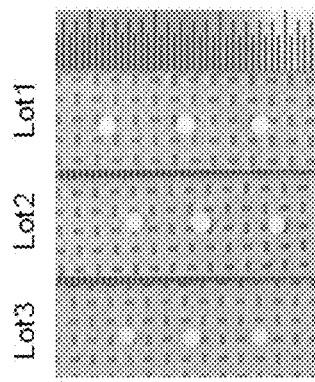
FIGS. 6a to 6f are results of evaluating properties of bead-type cartilage tissue (pellet) which was prepared by three-dimensional pellet culturing rabbit chondrocytes ($1.0 \times 10^5$/well) in a 96-well deep well plate having V-shaped bottom for 10 days.
Figure 6B:
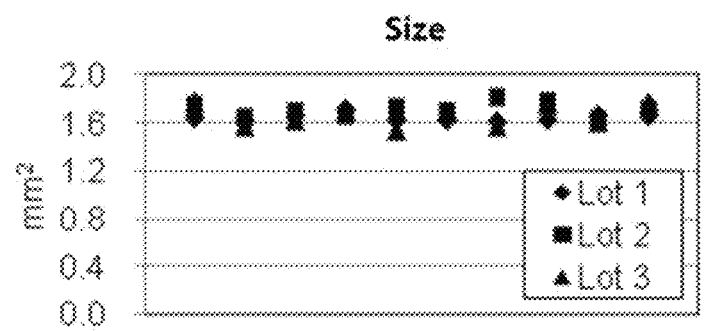
Figure 6C:
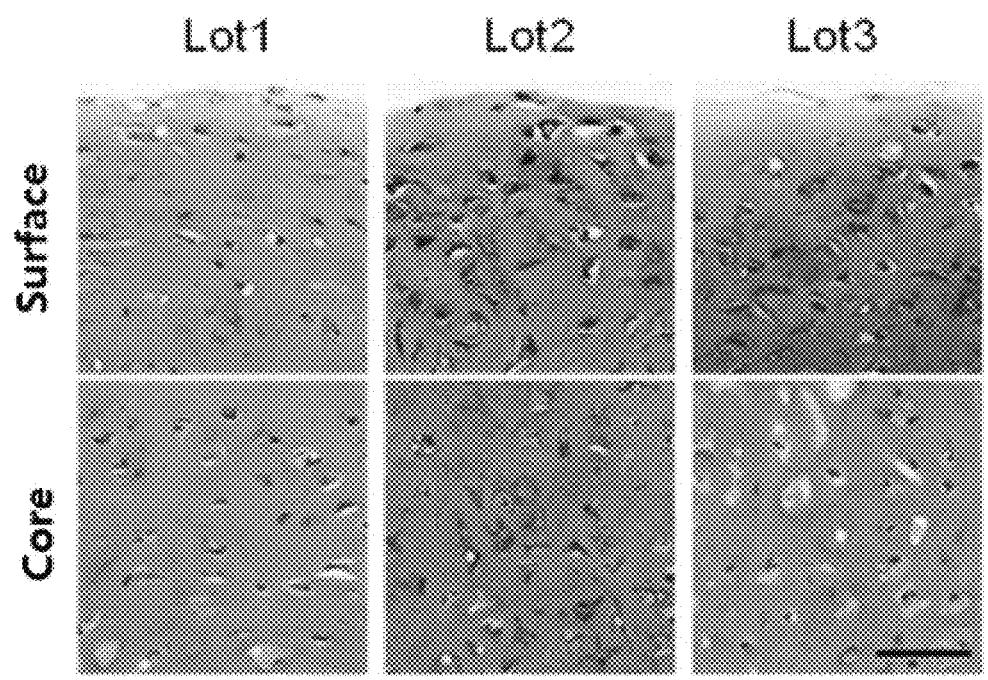
Figure 6D:
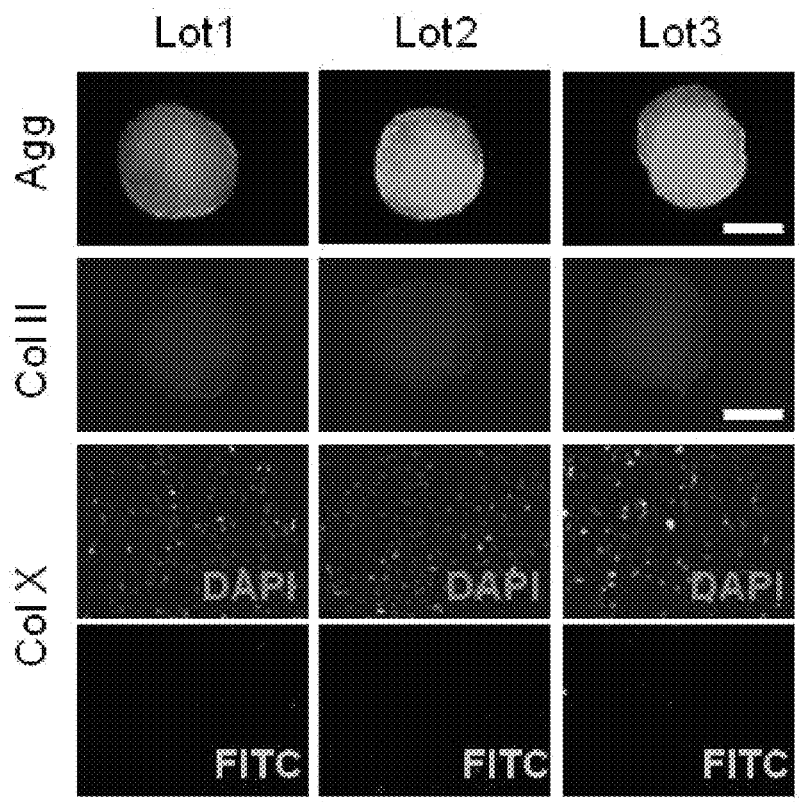
Figure 6E:
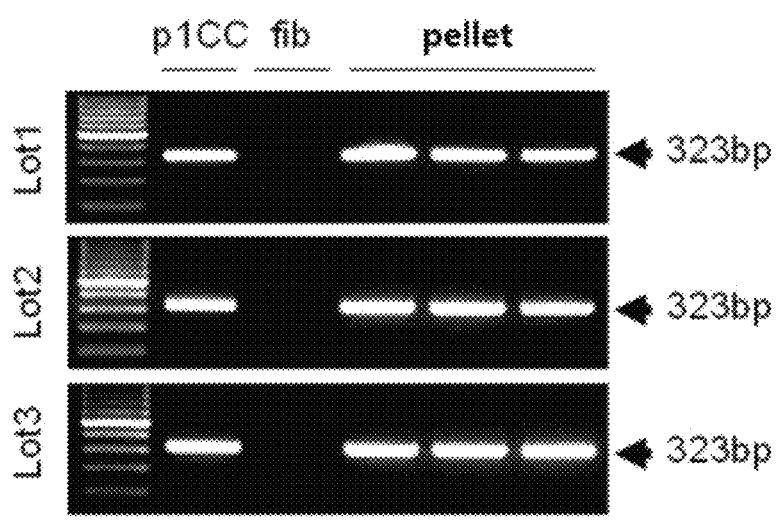
Figure 6F:
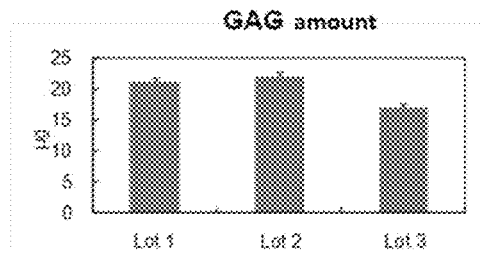

As a result, semitranslucent bead-type three-dimensional structures having white and smooth surface with the naked eye and 1.0 to 1.5 mm of diameter were observed (FIG. 6a). Their plane sizes were in the range of 1.6 mm²±20%, and the formation of uniform pellets in each well of 96-well deep well plate irrespective of cell-supplying subjects was observed (FIG. 6b). Cells existed in lacunae, and strong GAG expression was observed on the entire pellet (FIG. 6c). As a result of immunofluorescence staining, aggrecan was strongly stained on the entire pellet, but type II collagen was weakly stained on the entire pellet and the expression of type X collagen was hardly observed (FIG. 6d). As a result of evaluating the expression of type II collagen gene, all 3 lots expressed it (FIG. 6e). The cell viability in pellets was 95% or more, and the content of GAG was 15 to 30 μg/pellet (FIG. 6f).

Example 4

Human costal chondrocytes cultured in a culture medium for cell proliferation to passages 6 to 8 were suspended in a culture medium for differentiation and dispensed into a 96-well deep well plate having V-shaped bottom with 1.0×10⁵ cells/400 μl/well. The plates were centrifuged at 1,200 rpm for 5 minutes, and then pellet cultured in a 37° C., 5% $CO_2$ incubator for 10 days with exchanging culture media at an interval of 3 or 4 days to prepare a bead-type cartilage tissue without a scaffold for transplanting to articular cartilage damage. After culturing, the bead-type cartilage tissue was collected by the use of portable pellet collection apparatus (FIG. 8c), and properties were evaluated according to the methods described in Example 2.

Figure 7A:
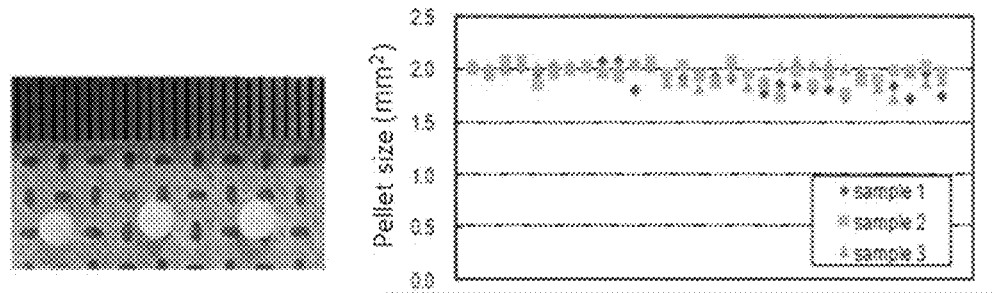
FIGS. 7a to 7f are results of evaluating properties of bead-type cartilage tissue (pellet) which was prepared by three-dimensional pellet culturing human chondrocytes ($1.0 \times 10^5$/well) in a 96-well deep well plate having V-shaped bottom for 10 days.
Figure 7B:
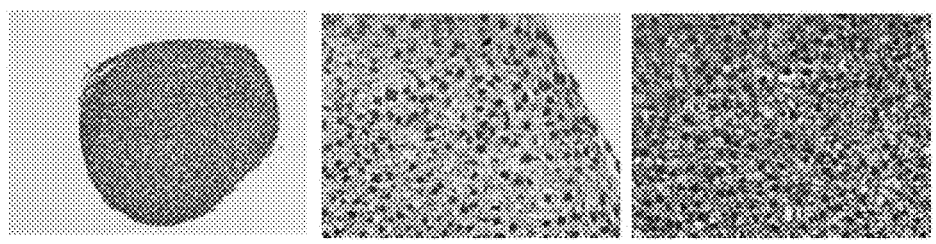
Figure 7C:
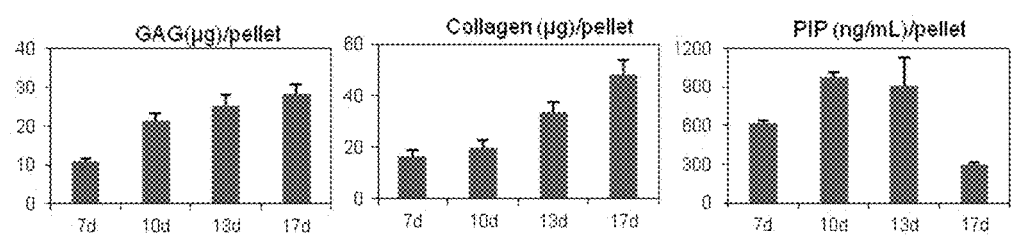
Figure 7D:
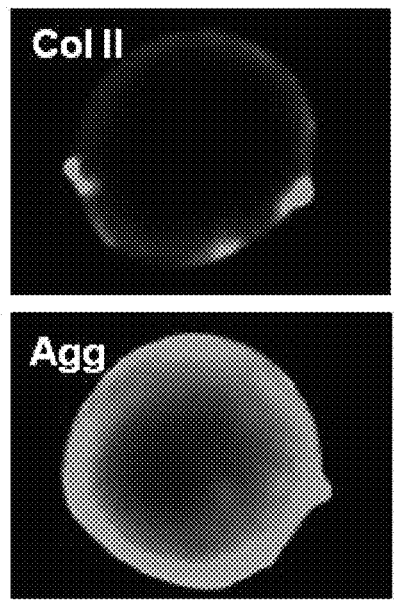
Figure 7E:
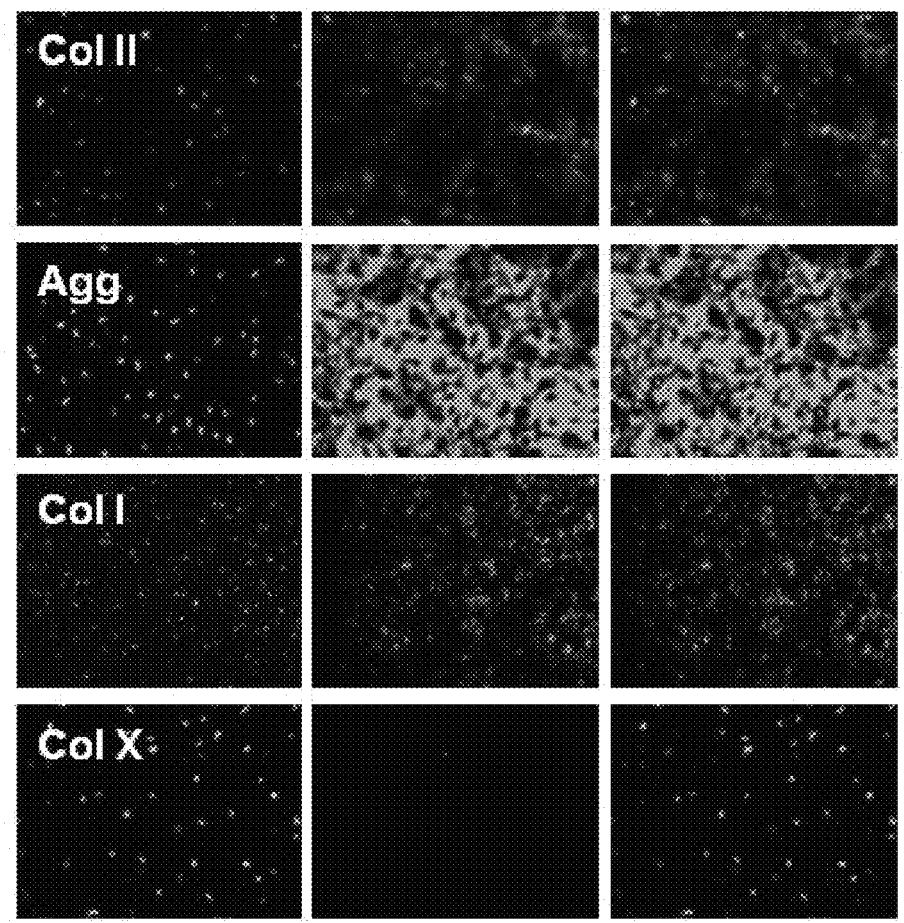
Figure 7F:
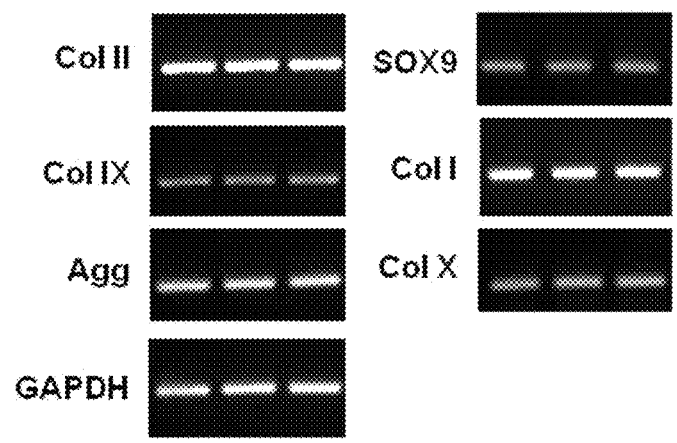

As a result, semitranslucent, small bead-type three-dimensional structures having white and smooth surface and 1.0 to 1.5 mm in diameter were obtained. As a result of measuring the size of 30 beads per lot, it can be known that the size is uniform (FIG. 7a). Histologically, cells were enveloped in matrix which strongly expresses GAG, existed in high density, and showed the morphology of immature chondrocytes (FIG. 7b). As a result of the three-dimensional culture until additional 17 days, the GAG and collagen amounts were continuously increased, but the procollagen type I C-peptide (PIP) amount was decreased after the 10$^{th}$ day (FIG. 7c). As a result of evaluating the expression of type II collagen and aggrecan, which are specific markers of hyaline cartilage cells, by fluorescence staining, although expression was weak, the expression of type II collagen through the entire pellet was observed, and aggrecan was strongly expressed on the entire pellet (FIG. 7d). As a result of evaluating the expression of type II collagen and aggrecan (hyaline cartilage cell-specific markers), type I collagen (immature chondrocyte-specific marker) and type X collagen (hypertrophic chondrocyte-specific marker) in a thin section of the pellet, the expression ratio was about 54%, 99%, 81% and 0%, respectively (FIG. 7e). As a result of evaluating gene expression by RT-PCR, the strong expression of type II collagen, type IX collagen and aggrecan—which are chondrocyte-specific markers—was observed, and the expression of sox-9—which is a transcription factor of chondrocyte—was also observed. In addition, the expression of type I collagen—which is a marker of immature chondrocyte—was observed, and the weak expression of type X collagen—which is a hypertrophic chondrocyte-specific marker—was observed (FIG. 7f).

Example 5

Figure 9A:
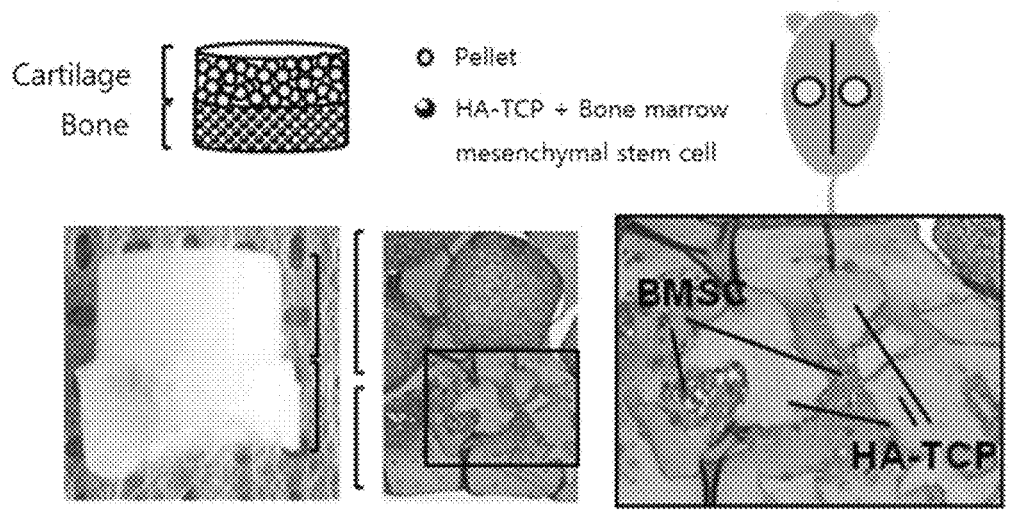
FIGS. 9a to 9d are photographs showing results wherein the pellets prepared from human chondrocytes of FIG. 7 were implanted under the skin of nude mice and observed after 4, 8, 16 and 20 weeks.

Animal Implantation Evaluation of Bead-type Cartilage Tissue: Nude Mouse Subcutaneous Implantation Human costal chondrocytes were proliferated to passages 6 to 8 and dispensed into a 96-well deep well plate having V-shaped bottom with 1.0×10⁵ cells/400 μl/well. After centrifugation, pellet culture was carried out in a culture medium for chondrogenic differentiation for 10 days. 40 pellets and fibrin glue (Greenplast™, Green Cross Corp., Korea) for pellet fixation were mixed to prepare a cartilage part, and a bone part—which was prepared by mixing HA-TCP (hydroxyapatite-tricalcium phosphate; PURUGO, Korea) and bone marrow-derived mesenchymal stem cells (BMSCs)—was placed below the cartilage part to prepare a cartilage-bone bilayer structure in the form of a sandwich for evaluating integration between bone and cartilage which is regenerated (FIG. 9a).

Anesthesia of animals was induced by xylazine and ketamine, and the operation region was prepared with alcohol and povidone-iodine. The central region of skin below the scapula of the prepared nude mice was incised about 1 cm, and the incised part was bluntly separated to the left side and right side to make pocket for implantation. Then, each of the bilayer structures was implanted into the left and right subcutaneously. On the 4$^{th}$ week, 8$^{th}$ week, 16$^{th}$ week and 20$^{th}$ week after implantation, animals were euthanized, and the skin of back and shoulder was then incised so the implants could be observed with the naked eye. In addition, the bone part and cartilage parts were pulled with a pair of forceps to evaluate the degree of their integration. The implants were fixed with 10% neutral buffered formalin, demineralized, embedded in paraffin, and sectioned at the thickness of 6 μm. Hematoxylin/eosin staining of the slice attached to a slide was carried out for histological evaluation, and immunostaining for type II collagen and aggrecan was carried out. In addition, to evaluate terminal differentiation immunostaining for type X collagen, which is a hypertrophic chondrocyte marker, was carried out.

Figure 9B:
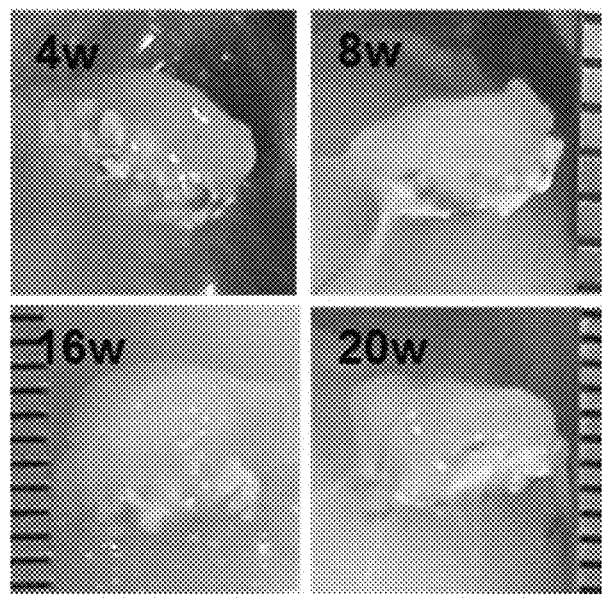
Figure 9C:
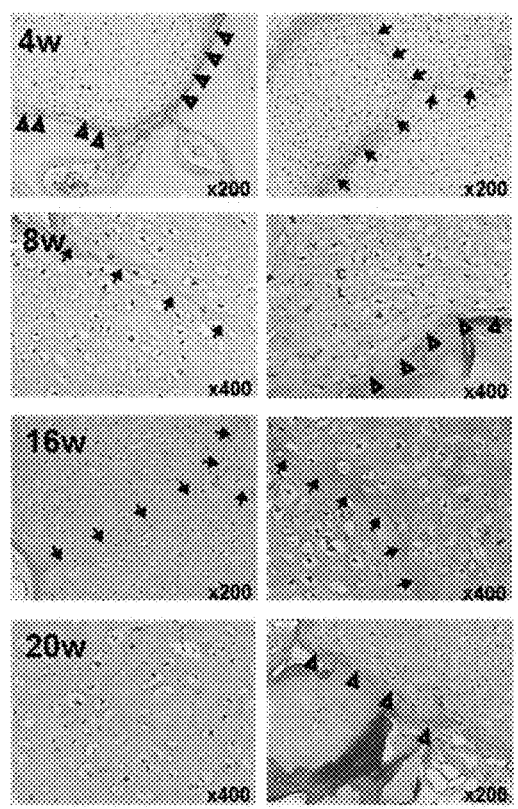
Figure 9D:
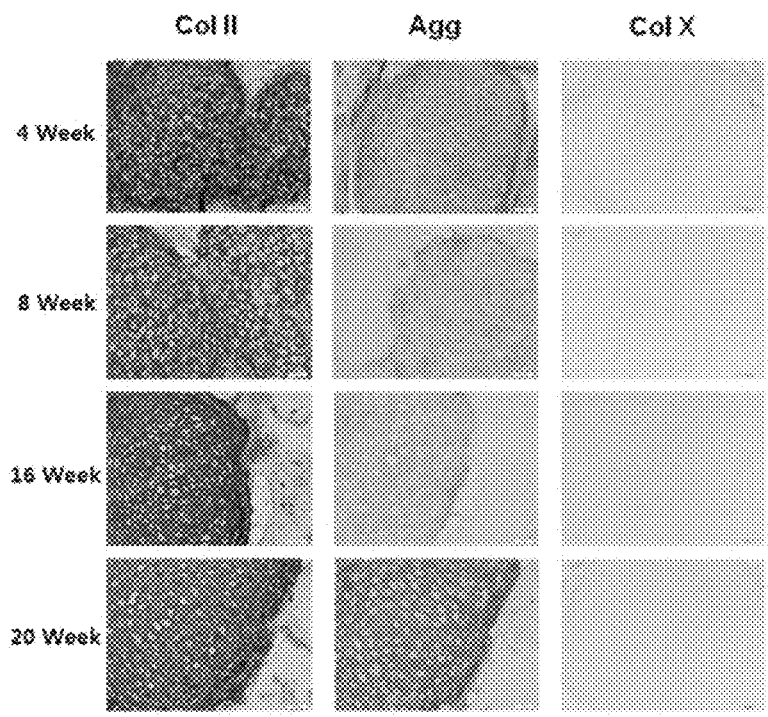

As a result, two layers of the implant structure were strongly integrated; the cartilage layer showed smooth surface, whiteness and semitranslucence like hyaline cartilage as observed with the naked eye; and the invasion of blood vessels was not observed. On the other hand, in the bone layer the invasion of blood vessels was observed (FIG. 9b). Histologically, the pellets were well merged with each other, and their integration with bone matrix was also observed (FIG. 9c). Type II collagen—which is a hyaline cartilage-specific marker—was strongly expressed from the $4^{th}$ week to the $20^{th}$ week after implantation, and the expression of aggrecan showed the tendency of decreasing and then increasing again. The expression of type X collagen, which is a hypertrophic chondrocyte marker, was not observed until the $20^{th}$ week (FIG. 9d).

Example 6

Figure 10A:
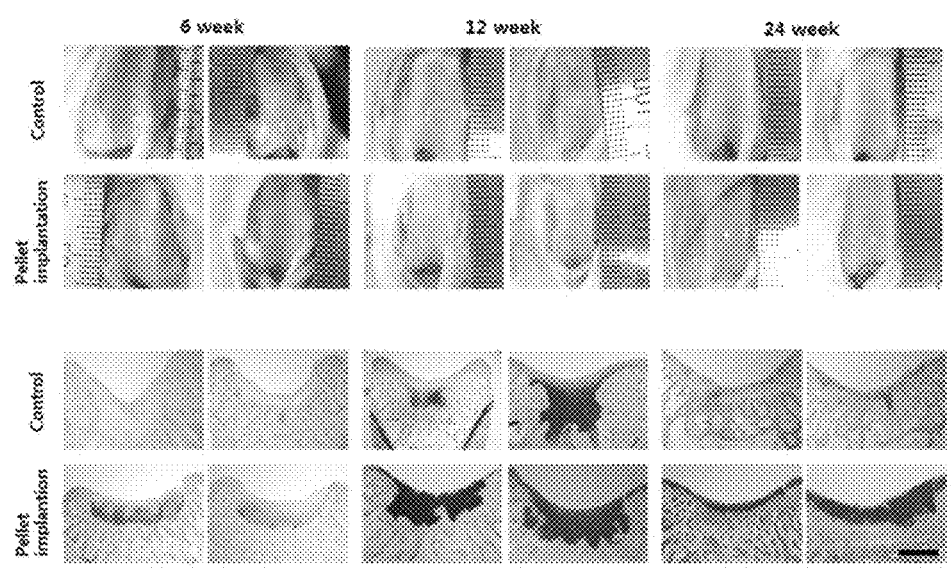
FIGS. 10a to 10c are results wherein the pellets prepared from rabbit chondrocytes of FIG. 6 were implanted into the damaged area of rabbit knee cartilage and the regenerated tissues of implantation area were observed after 6, 12 and 24 weeks.
Figure 10B:
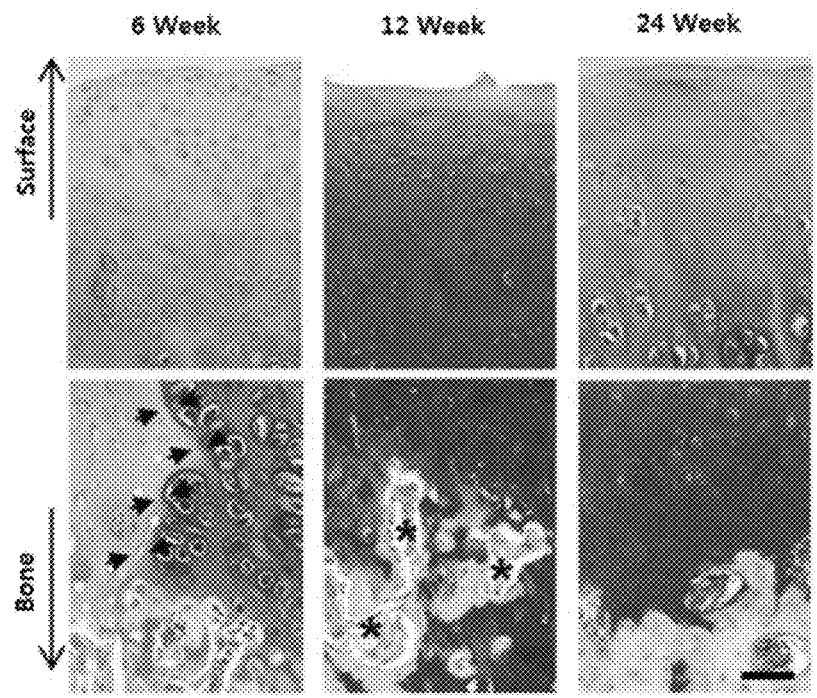
Figure 10C:
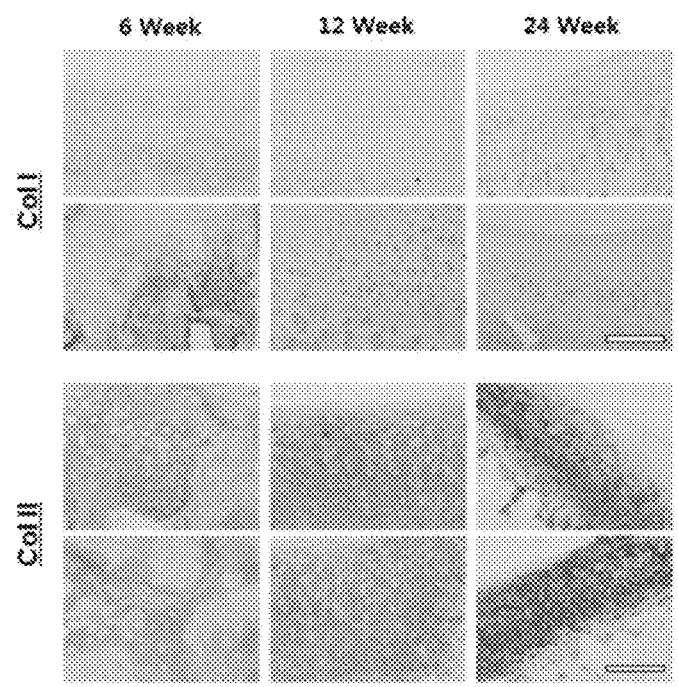

Animal Implantation Evaluation of Bead-type Cartilage Tissue: Rabbit Knee Cartilage Damaged Area Implantation Rabbit costal chondrocytes were proliferated to passages 6 to 8 and dispensed into a 96-well deep well plate having V-shaped bottom with $1.0 \times 10^5$ cells/400 μl/well. After centrifugation, pellet culture was carried out in a culture medium for chondrogenic differentiation for 10 days. The medial parapatellar incision of rabbit knee was made to expose the patellar groove, and cartilage damage of the diameter of 5 mm and the depth of about 2 mm was made with a dental micro-drill. After removal of detached fragments by strongly washing the damaged area with a cold saline solution, 18 to 20 pellets were equally mixed with fibrinogen and diluted thrombin (about 10 IU), and the resulting mixture was then immediately implanted into the cartilage damage. Fibrin glue comprising high concentration of thrombin was applied thereon. In the control damage, only fibrin glue (Greenplast™, Green Cross Corp., Korea) was used. After sufficient solidification, the patella went back to the original position, and the joint capsule and skin were sutured. On the $6^{th}$ week, $12^{th}$ week and $24^{th}$ week after implantation, the operated knee was incised to observe the joint capsule and knee cartilage with the naked eye, and the distal femoral epiphysis was cut. The prepared sample was fixed with 10% neutral buffered formalin, demineralized, embedded in paraffin, and sectioned at the thickness of 6 μm, and Safranin O staining and immunostaining for type I collagen or type II collagen were carried out. As a result, the repair of the damaged area to hyaline cartilaginous tissue was confirmed with the naked eye, histologically and immunochemically (FIG. 10).

Example 7

Animal Implantation Evaluation of Bead-type Cartilage Tissue: Goat Knee Cartilage Damaged Area Implantation Goat costal chondrocytes were proliferated to passages 6 to 8 and dispensed into a 96-well deep well plate having V-shaped bottom with $1.0 \times 10^5$ cells/400 μl/well. After centrifugation, pellet culture was carried out in a culture medium for chondrogenic differentiation for 10 days. The medial parapatellar incision of goat knee was made to expose the patellar groove and medial femoral condyle, and cartilage damage of the diameter of 8 mm and the depth of about 2 mm was made with a dental micro-drill. After removal of detached fragments by strongly washing the damaged area with a cold saline solution, about 48 pellets were fixed to the damaged area by the use of fibrin glue (about 10 IU of thrombin) or autologous platelet rich plasma (PRP) obtained by the centrifugation of the blood and thrombin (about 10 IU). And then, fibrin glue comprising high concentration of thrombin or autologous PRP was applied on the surface. After sufficient solidification, the patella went back to the original position, and the joint capsule and skin were sutured. To confirm cellular fixation at the damaged area after cell transplantation, on the $2^{nd}$ week MRI (Magnus 2.1 for Magnum 3.0T MRI system; Medinus, Korea) evaluation on both knees of the goat was carried out. To evaluate the physical properties of the regenerated tissues immediately after implantation and on the $12^{th}$ week and the $24^{th}$ week after implantation, an indentation test was carried out by the use of a Universal Testing Machine (H5K-T, H.T.E., Salfords, UK). The knee area including the regenerated tissues was cut with a saw, and the central part of the regenerated tissues was indented to the depth of 400 μm with the velocity of 0.1 S-1 by the use of 5 N load cell and indenter probe having the diameter of 3 mm to measure stiffness and elastic modulus. The results are represented in Table 2.

TABLE 2

| Physical property | | Strength (kN/M) | Elasticity (kPa) |
|---|---|---|---|
| Normal cartilage | | 5.93 ± 1.05 | 838.68 ± 148.49 |
| Pellet implantation | Immediately after implantation | 0.66 ± 0.05 | 110.25 ± 8.17 |
| | $12^{th}$ week | 2.52 ± 0.72 | 356.32 ± 101.81 |
| | $24^{th}$ week | 4.93 ± 1.15 | 697.37 ± 162.22 |
| Fibrin glue alone | $24^{th}$ week | 1.997 | 282.60 |

As can be seen from Table 2, even immediately after implantation the strength was about ⅛ of that of normal cartilage, and on the $12^{th}$ week and $24^{th}$ week after implantation the stiffness and elastic modulus were about ½ and similar level to those of the normal cartilage, respectively.

REFERENCES

Adkisson H D, Gillis M P, Davis E C, Maloney W, Hruska K A. In vitro generation of scaffold independent neocartilage. Clin Orthop 2001; 391S:S280-94

Anderer U, Libera J. In vitro engineering of human autologous cartilage. J Bone Miner Res 2002; 17: 1420-29.

Brittberg M, Lindahl A, Nilsson A, Ohlsson C, Isaksson O, Peterson L. Treatment of deep cartilage defects in the knee with autologous chondrocyte transplantation. N Engl J Med. 1994 Oct. 6; 331(14):889-95.

Cancedda R, Dozin B, Giannoni P, Quarto R. Tissue engineering and cell therapy of cartilage and bone. Matrix Biology. 2003; 22:81-91.

Choi Y Y, Chung B G, Lee D H, Khademhosseini A, Kim J H, Lee S H. Controlled size embryoid body formation in concave microwell arrays. Biomaterials 2010; 31:4296-303.

Croucher L J, Crawford A, Hatton P V, Russell R G, Buttle D J. Extracellular ATP and UTP stimulate cartilage proteoglycan and collagen accumulation in bovine articular chondrocyte pellet cultures. Biochim Biophys Acta 2000; 1502: 297-306.

Fukuda J, Nakazawa K. Orderly arrangement of hepatocyte spheroids on a microfabricated chip. Tissue Eng 2005; 11:1254-62.

Graff R D, Lazarowski E R, Banes A J, Lee G M. ATP release by mechanically loaded porcine chondrons in pellet culture. Arthritis Rheum 2000; 43:1571-9.

Grande D A, Halberstadt C, Naughton G, Schwartz R, Manji R. Evaluation of matrix scaffolds for tissue engineering of articular cartilage grafts. J Biomed Mater Res 1997; 34:211-20.

Grogan S P, Rieser B, Winkelmann H F P, Berardi S, Mainil-Varlet P. A static, closed and scaffold-free bioreactor system that permits chondrogenesis in vitro. Osteoarthritis Cartilage 2003; 11:403-11.

Hutmacher D W. Scaffolds in tissue engineering bone and cartilage. Biomaterials 2000; 21:2529-43.

Imabayashi H, Mori T, Gojo S, Kiyono T, Sugiyama T, Irie R, Isogai T, Hata J, Toyama Y, Umezawa A. Redifferentiation of dedifferentiated chondrocytes and chondrogenesis of human bone marrow stromal cells via chondrosphere formation with expression profiling by large-scale cDNA analysis. Exp Cell Res 2003; 288(1):35-50.

Jain R K, Au P, Tam J, Duda D G, Fukumura D. Engineering vascularized tissue. Nat Biotechnol 2005; 23:821-3.

Landry J, Freyer J P. Regulatory mechanisms in spheroidal aggregates of normal and cancerous cells. Recent Results Cancer Res 1984; 95: 50-66.

Landry J, Bernier D, Ouellet C, Goyette R, Marceau N. Spheroidal aggregate culture of rat liver cells: histotypic reorganization, biomatrix deposition, and maintenance of functional activities. J Cell Biol 1985; 101: 914-23.

Larson C M, Kelley S S, Blackwood A D, Banes A J, Lee G M. Retention of the native chondrocyte pericellular matrix results in significantly improved matrix production. Matrix Biol 2000; 21:349-59.

Marlovits S, Tichy B, Truppe M, Gruber D, Vecsei V. Chondrogenesis of aged human articular cartilage in a scaffold-free bioreactor. Tissue Eng 2003; 9:1215-26.

Moscona A. Rotation-mediated histogenetic aggregation of dissociated cells. A quantifiable approach to cell interactions in vitro. Exp Cell Res 1961; 22: 455-475.

Naumann A, Dennis J E, Aigner J, Coticchia J, Arnold J, Berghaus A, Kastenbauer E R, Caplan Al. Tissue engineering of autologous cartilage grafts in three-dimensional in vitro macroaggregate culture system. Tissue Eng 2004; 10(11-12):1695-706.

Nehrer S, Breinan H A, Ramappa A, Hsu H P, Minas T, Shortkroff S, Sledge C B, Yannas I V, Spector M. Chondrocyte seeded collagen matrices implanted in a chondral defect in a canine model. Biomaterials 1998; 19:2313-28.

Ochi M, Uchio Y, Tobita M, Kuriwaka M. Current concepts in tissue engineering technique for repair of cartilage defect. Artif Organs 2001; 25:172-9.

Park K, Huang J, Azar F, Jin R L, Min B H, Han D K, Hasty K. Scaffold-free, engineered porcine cartilage construct for cartilage defect repair-in vitro and in vivo study. Artif Organs 2006; 30(8): 586-96.

Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. Science 1999; 284(5411): 143-7.

Reginato A M, Iozzo R V, Jimenez S A. Formation of nodular structures resembling mature articular cartilage in long-term primary cultures of human fetal epiphyseal chondrocytes on a hydrogel substrate. Arthritis Rheum 1994; 7:1338-49.

Rouwkema J. Rivron N C. van Blitterswijk C A. Vascularization in tissue engineering. Trends Biotechnol 2008; 26:434.

Sims C D, Butler P E, Cao Y L, Casanova R, Randolph M A, Black A, Vacanti C A, Yaremchuk M J. Tissue engineered neocartilage using plasma derived polymer substrates and chondrocytes. Plast Reconstr Surg 1998; 101:1580-5.

Sittinger M, Reitzel D, Dauner M, et al. Resorbable polyesters in cartilage engineering: affinity and biocompatibility of polymer fiber structures to chondrocytes. J Biomed Mater Res 1996; 33:57-63.

Stewart M C, Saunders K M, Burton-Wurster N, Macleod J N. Phenotypic stability of articular chondrocytes in vitro: the effects of culture models, bone morphogenetic protein 2, and serum supplementation. J Bone Miner Res 2000 January; 15(1):166-74.

Tavella S, Bellese G, Castagnola P, Martin I, Piccini D, Doliana R, Colombatti A, Cancedda R, Tacchetti C. Regulated expression of fibronectin, laminin and related integrin receptors during the early chondrocyte differentiation. J Cell Sci 1997; 110:2261-70.

Wolf F, Candrian D, Wendts D, Farhadi J, Heberer M, Martin I, Barbero A. Cartilage tissue engineering using pre-aggregated human articular chondrocytes. European Cells and Materials 2008; 16:92-99.

Wong S F, No da Y, Choi Y Y, Kim D S, Chung B G, Lee S H. Concave microwell based size-controllable hepatosphere as a three-dimensional liver tissue model. Biomaterials. 2011 November; 32(32):8087-96.

Zhang Z, McCaffery M, Spencer R G, Francomano C A. Hyaline cartilage engineered by chondrocytes in pellet culture: histological, immunohistochemical and ultrastructural analysis in comparison with cartilage explants. J Anat 2004; 205:229-37.

What is claimed is:

1. A method for preparing a therapeutic agent of bead-type chondrocyte which comprises the following steps:
    a) dispensing chondrocyte and/or cell having chondrogenic potential into a 96-well deep well plate having V-shaped bottom and well volume of 500 µl or more, with $0.5 \times 10^5$ cells to $2.0 \times 10^5$ cells/400 to 600 µl/well;
    b) centrifuging the plate;
    c) three-dimensionally culturing the plate in an incubator; and
    d) collecting a pellet from each well.

2. The method for preparing a therapeutic agent of bead-type chondrocyte according to claim 1, wherein the cell having chondrogenic potential in step (a) is selected from the group consisting of mesenchymal stem cell, embryonic stem cell and induced pluripotent stem cell.

3. The method for preparing a therapeutic agent of bead-type chondrocyte according to claim 2, wherein the mesenchymal stem cell is adipose-derived, bone marrow-derived, umbilical cord-derived, umbilical cord blood-derived, placenta-derived, synovium-derived, periosteum-derived or perichondrium-derived cell.

4. The method for preparing a therapeutic agent of bead-type chondrocyte according to claim 1, wherein said chondrocyte or cell is dispensed with $0.5 \times 10^5$ cells to $2.0 \times 10^5$ cells/400 µl/well in step (a).

5. The method for preparing a therapeutic agent of bead-type chondrocyte according to claim 1, wherein said chondrocyte or cell is dispensed by the use of an apparatus selected from the group consisting of a multi-channel pipette, a multi-pipette, a microplate washer and a microplate dispenser in step (a).

6. The method for preparing a therapeutic agent of bead-type according to claim 1, wherein the centrifugation is carried out at 500 to 3,000 rpm for 5 to 10 minutes in step (b).

7. The method for preparing a therapeutic agent of bead-type chondrocyte according to claim 1, wherein the three-dimensional culture is carried out in a serum-free culture medium in step (c).

8. The method for preparing a therapeutic agent of bead-type chondrocyte according to claim 1, wherein the three-dimensional culture is carried out for 3 days to 30 days in step (c).

9. The method for preparing a therapeutic agent of bead-type chondrocyte according to claim 1, which further comprises a step of exchanging a culture medium in step (c).

10. The method for preparing a therapeutic agent of bead-type chondrocyte according to claim 9, wherein the exchange of culture medium is carried out by the use of an apparatus selected from the group consisting of a multi-channel pipette, a multi-pipette, a microplate washer and a microplate dispenser.

* * * * *